US012629189B2

(12) United States Patent
Phillips

(10) Patent No.: US 12,629,189 B2
(45) Date of Patent: May 19, 2026

(54) RIB PLATING AND FIXATION SYSTEM AND METHOD

(71) Applicant: DEPUY SYNTHES PRODUCTS, INC., Raynham, MA (US)

(72) Inventor: Emma Phillips, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 225 days.

(21) Appl. No.: 18/356,383

(22) Filed: Jul. 21, 2023

(65) Prior Publication Data

US 2024/0041507 A1 Feb. 8, 2024

Related U.S. Application Data

(60) Provisional application No. 63/370,297, filed on Aug. 3, 2022.

(51) Int. Cl.
*A61B 17/80* (2006.01)
*A61B 17/56* (2006.01)

(52) U.S. Cl.
CPC .......... *A61B 17/8076* (2013.01); *A61B 17/56* (2013.01); *A61B 2017/564* (2013.01)

(58) Field of Classification Search
CPC ............ A61B 17/7049; A61B 17/7052; A61B 17/8076
See application file for complete search history.

(56) References Cited

U.S. PATENT DOCUMENTS

| | | | |
|---|---|---|---|
| 8,956,392 B2 | 2/2015 | Khatchadourian | |
| 8,974,500 B2 | 3/2015 | Khatchadourian | |
| 9,468,467 B2 * | 10/2016 | Rathbun | A61B 17/707 |
| 9,526,524 B2 | 12/2016 | Khatchadourian | |
| 10,010,352 B2 | 7/2018 | Khatchadourian | |
| 2004/0153067 A1 | 8/2004 | Smith | |
| 2008/0082101 A1 | 4/2008 | Reisberg | |
| 2013/0090695 A1 * | 4/2013 | Bernstein | A61B 17/808 |
| | | | 606/281 |
| 2014/0222074 A1 * | 8/2014 | Rathbun | A61B 17/705 |
| | | | 606/258 |
| 2015/0209093 A1 * | 7/2015 | Dallis | A61B 17/8061 |
| | | | 606/281 |

(Continued)

FOREIGN PATENT DOCUMENTS

| | | |
|---|---|---|
| EP | 2997916 A1 | 3/2016 |
| EP | 3747384 A1 | 12/2020 |

OTHER PUBLICATIONS

International Search Report & Written Opinion for PCT/IB2023/057870 mailed on Nov. 22, 2023.

(Continued)

*Primary Examiner* — Tessa M Matthews
(74) *Attorney, Agent, or Firm* — Kramer & Amado, P.C.

(57) ABSTRACT

A rib fixation system, including: a rib plate having a plurality of screw holes; a first ring component with a screw hole and ridge; a second ring component with a screw hole and a slot configured to receive a portion of the first ring component; and a screw configured to be placed through one of the plurality of screw holes of the rib plate, the screw hole of the first ring, and the screw hole of the second ring, wherein the ridge of the first ring provides a stop for the second ring.

12 Claims, 15 Drawing Sheets

(56) References Cited

U.S. PATENT DOCUMENTS

2020/0337750 A1 * 10/2020 Hu ..................... A61B 17/7056
2024/0090925 A1 * 3/2024 Zhang ................ A61B 17/7032

OTHER PUBLICATIONS

International Preliminary Report on Patentability for corresponding PCT Application No. PCT/IB2023/057870 mailed on Feb. 4, 2025.
"Vertical Expandable Prosthetic Titanium Rib II (Veptr II) Surgical Technique", DePuy Synthes, Nov. 2016.

* cited by examiner

100
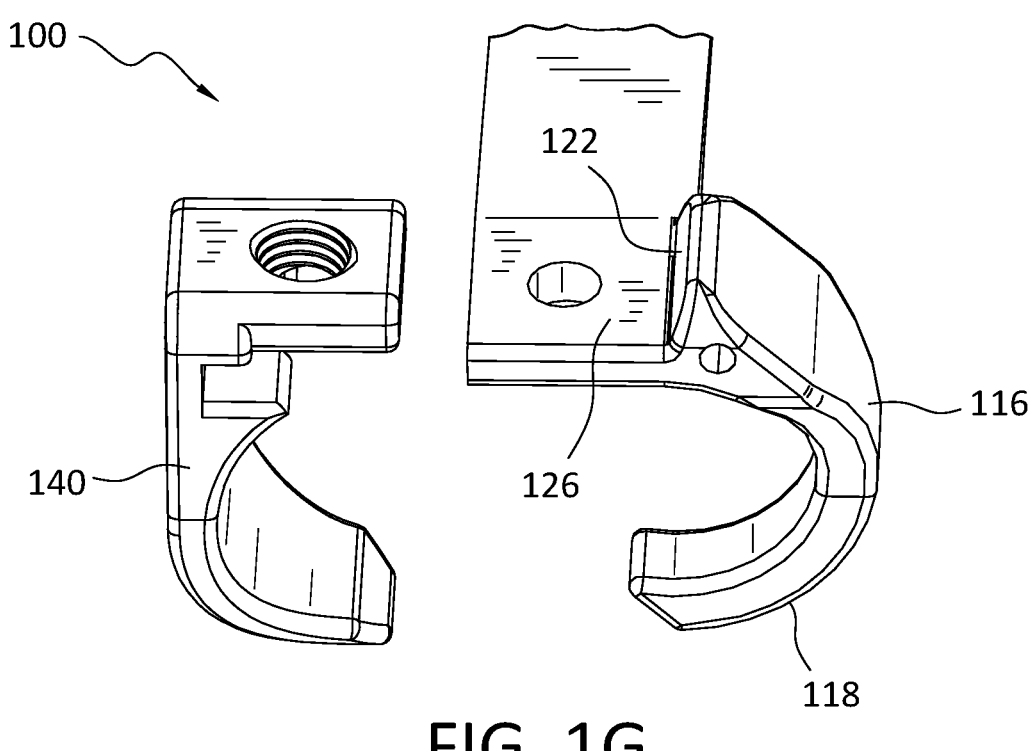
122
126
116
140
118
FIG. 1G
100
128
116
140
118
FIG. 1H
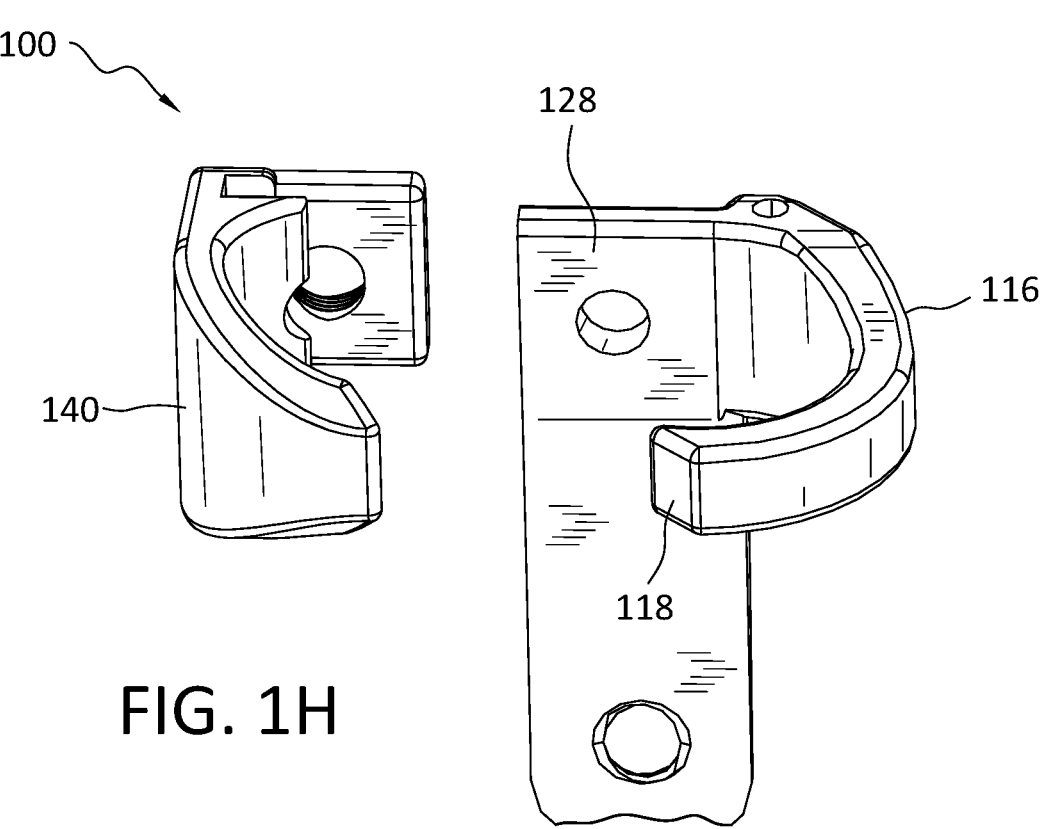

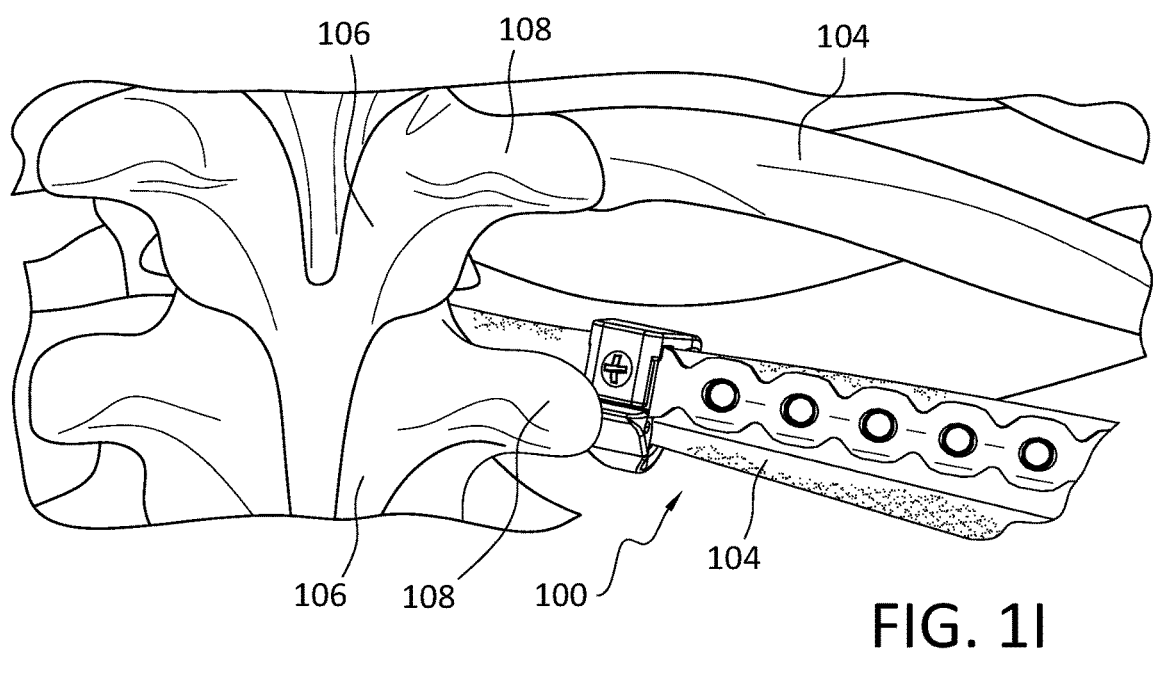
FIG. 1I
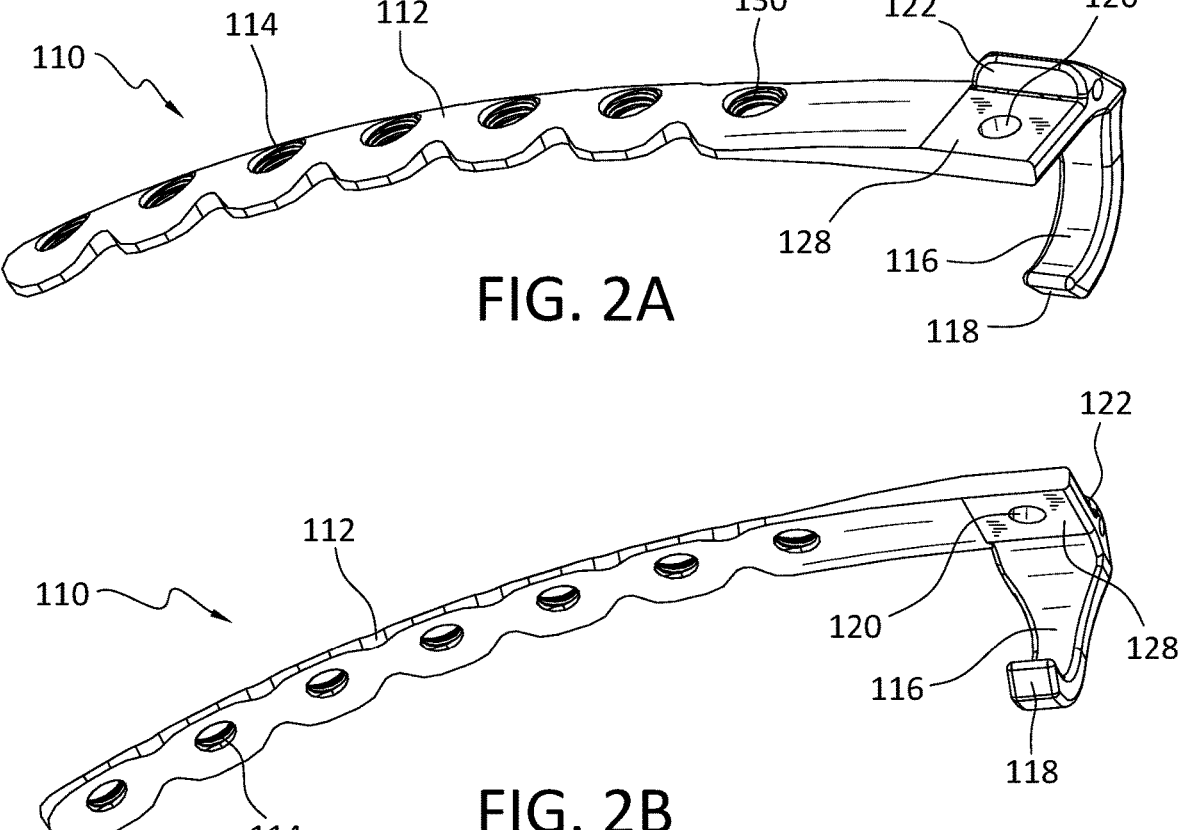
FIG. 2A
FIG. 2B

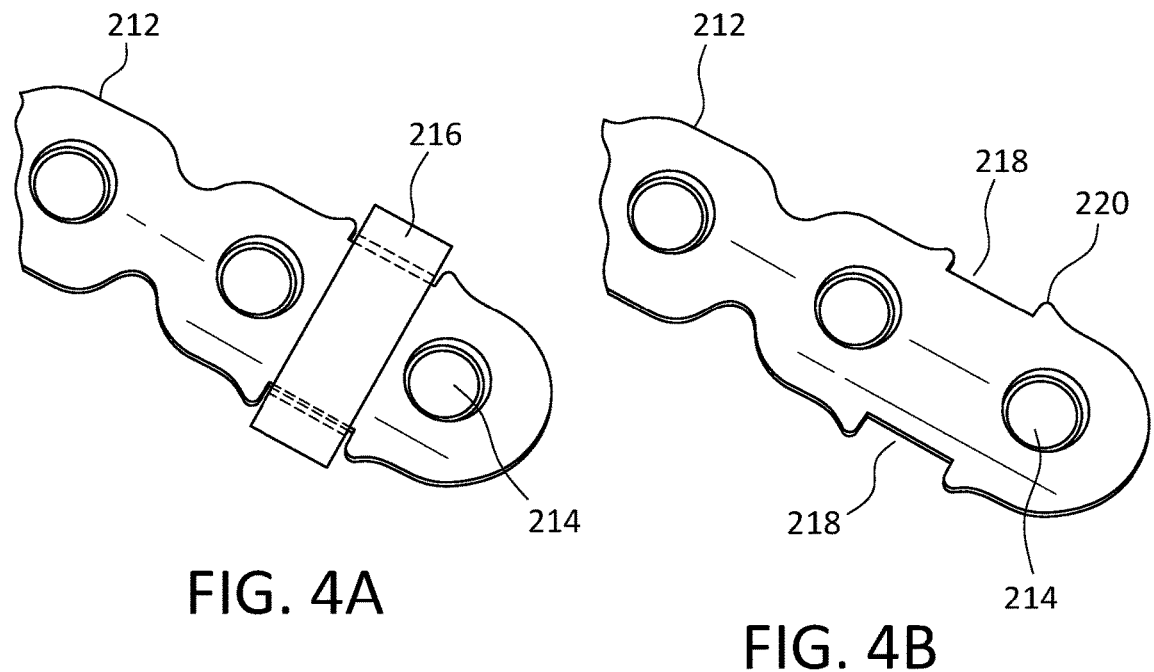
FIG. 4A
FIG. 4B
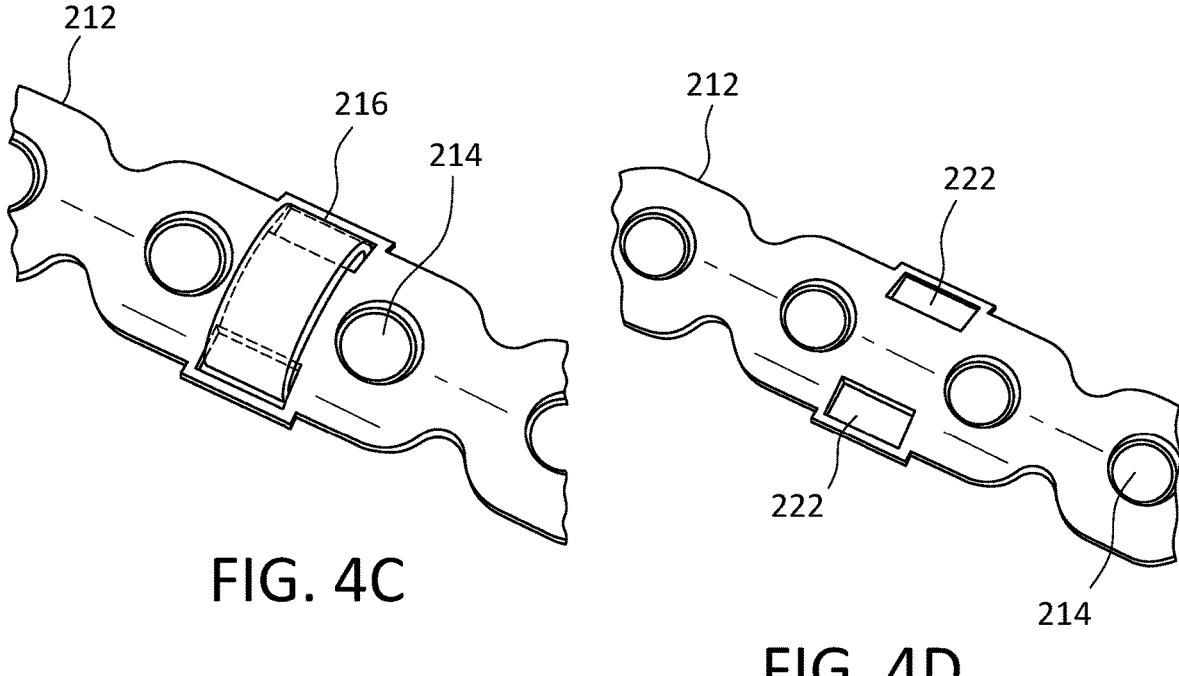
FIG. 4C
FIG. 4D

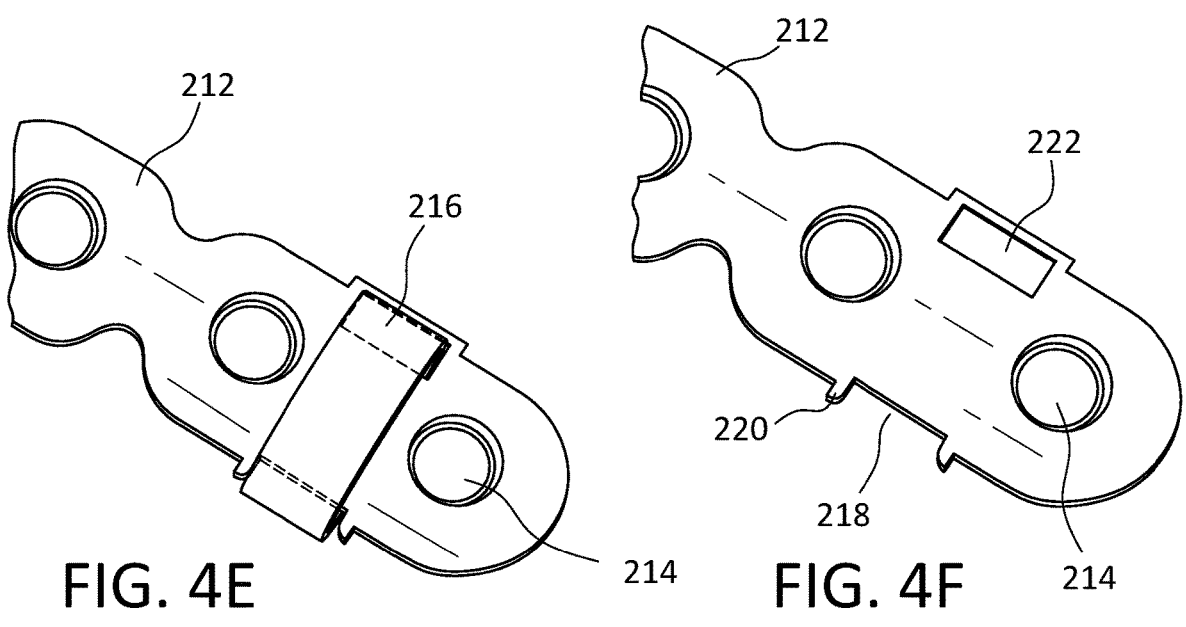
FIG. 4E
FIG. 4F
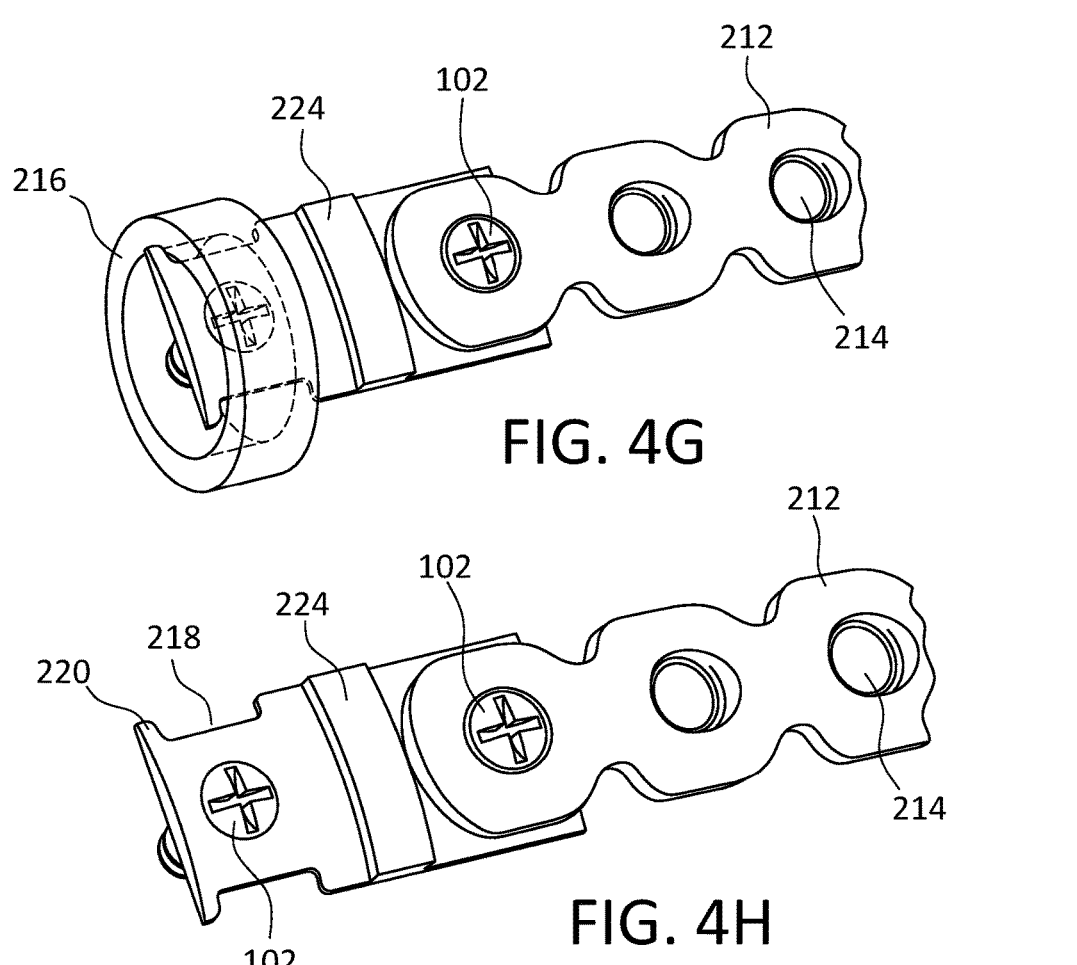
FIG. 4G
FIG. 4H

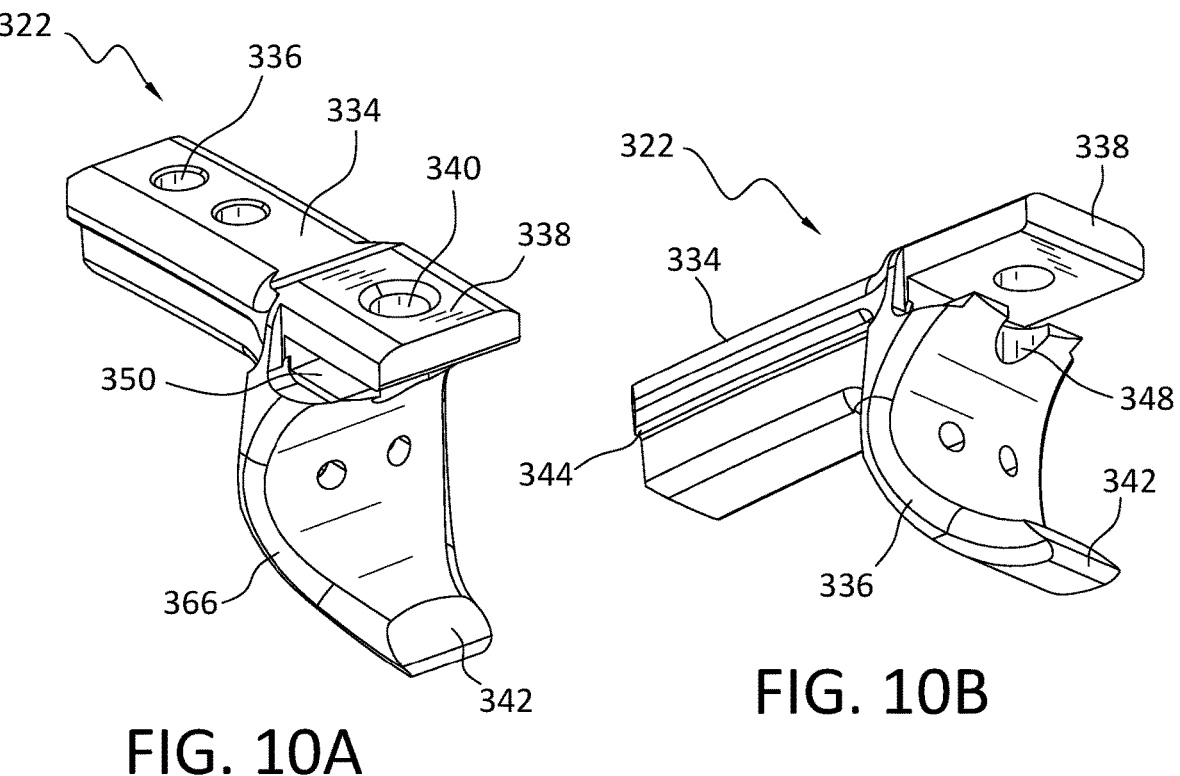
FIG. 10A
FIG. 10B
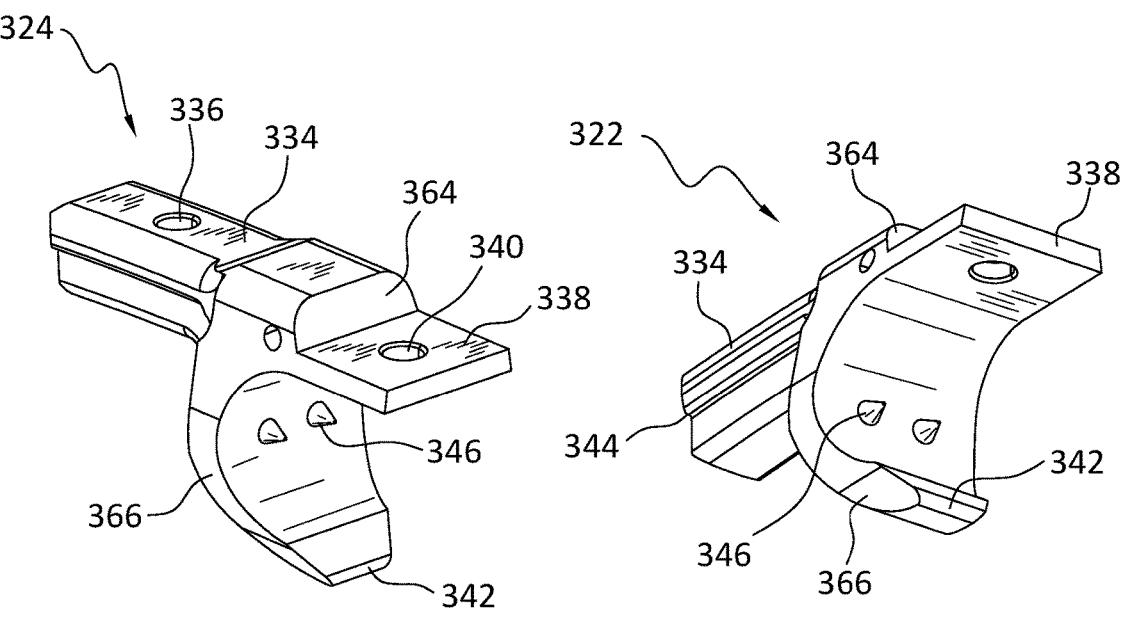
FIG. 11A
FIG. 11B

RIB PLATING AND FIXATION SYSTEM AND METHOD

CROSS-REFERENCE TO RELATED APPLICATION

This application claims the benefit of U.S. Provisional Patent Application No. 63/370,297, filed Aug. 3, 2022, which is incorporated, for all purposes, by reference herein in its entirety.

TECHNICAL FIELD

Various exemplary embodiments disclosed herein relate generally to a rib plating and fixation system and method.

BACKGROUND

Rib plates may be used to repair, fix, and align broken ribs. Plates are especially useful when a rib has more than one break. The rib plates help to facilitate healing of the rib by fixing broken rib portions to one another.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a rib fixation system, including: a rib plate having a plurality of screw holes; a first ring component with a screw hole and ridge; a second ring component with a screw hole and a slot configured to receive a portion of the first ring component; and a screw configured to be placed through one of the plurality of screw holes of the rib plate, the screw hole of the first ring component, and the screw hole of the second ring component, wherein the ridge of the first ring component provides a stop for the second ring component.

Various embodiments are described, wherein first ring is formed integral with the rib plate.

Various embodiments are described, wherein second ring is formed integral with the rib plate.

Various embodiments are described, wherein when a portion of the second ring component engages first ring component ridge of the first ring component and the screw hole of the second ring component align.

Various embodiments are described, wherein when a portion of the first ring component engages the slot of the first ring component and the screw hole of the second ring component align.

Various embodiments are described, wherein the slot is formed by a second ring arm and a second ring interface surface.

Various embodiments are described, wherein the second ring interface surface includes a screw notch.

Further various embodiments relate to a rib fixation system, including: a fixation tie; a rib plate having a plurality of screw holes and a first fixation structure on a first edge of the rib plate and a second fixation structure on a second edge of the rib plate, where the first fixation structure and the second fixation structure are configured to capture and engage the fixation tie; and a screw configured to be inserted into one of the plurality of screw holes.

Various embodiments are described, wherein the first fixation structure and second fixation structure are fixation slots.

Various embodiments are described, wherein the first fixation structure and second fixation structure are fixation openings.

Various embodiments are described, wherein the first fixation structure is a fixation opening and second fixation structure is a fixation slot.

Further various embodiments relate to a rib fixation system, including: a fixation tie; a rib plate including a plurality of screw holes; a rib plate extension including a first screw hole, a second screw hole, a first fixation structure on a first edge of the rib plate extension, and a second fixation structure on a second edge of the rib plate extension, where the first fixation structure and the second fixation structure are configured to capture and engage the fixation tie; a first screw configured to be inserted into one of the plurality of screw holes of the rib plate and the first screw hole of the rib plate extension; and a second screw configured to be inserted in to one of the plurality of screw holes of the rib plate.

Various embodiments are described, wherein the first fixation structure and second fixation structure are fixation slots.

Various embodiments are described, wherein the first fixation structure and second fixation structure are fixation openings.

Various embodiments are described, wherein the first fixation structure is a fixation opening and second fixation structure is a fixation slot.

Various embodiments are described, further comprising a third screw configured to be inserted in the second screw hole of the rib plate extension.

Further various embodiments relate to a rib fixation system, including: a rib plate having a plurality of screw holes; a first closure ring with a screw hole; a first cradle with a screw hole and a cradle mount configured to engage the first closure ring to form a first ring; a second cradle with a screw hole and cradle mount; a third cradle with a screw hole configured to engage the second cradle to form a second ring, wherein the second ring is configured to engage the rib plate; a first spanning segment configured to securely engage the cradle mount of the first cradle and the cradle mount of the second cradle; a first screw configured to be inserted through the screw hole of the first closure ring and the screw hole of the first cradle; and a second screw configured to be inserted through the screw hole of the first cradle and the screw hole of the second cradle.

Various embodiments are described, further including: a second closure ring with a screw hole; a fourth cradle with a screw hole and a cradle mount configured to engage the second closure ring to form a third ring; a second spanning segment configured to securely engage the cradle mount of the fourth cradle and a cradle mount of the third cradle; and a third screw configured to be inserted through the screw hole of the second closure ring and the screw hole of the fourth cradle.

Various embodiments are described, further comprising a locking clip configured to secure the first spanning segment to the first cradle.

Various embodiments are described, wherein the first spanning segment includes a plurality of holes, the cradle mount of the first cradle includes a hole, and the locking clip includes a post, wherein the post is configured to be inserted into one of the plurality of holes of the first spanning segment and the hole of the cradle mount of the first cradle.

Various embodiments are described, wherein the second cradle includes a slot configured to receive a portion of the third cradle, and the third cradle includes a ridge configured to provide a stop for the second cradle.

Various embodiments are described, wherein when a portion of the second cradle engages the ridge of the third cradle of the second cradle and the screw hole of the third cradle align.

Various embodiments are described, wherein when a portion of the third cradle engages the slot of the second cradle and the screw hole of the third cradle align.

Various embodiments are described, wherein the slot is formed by a second cradle arm and a second cradle interface surface.

Various embodiments are described, wherein the first cradle includes a slot configured to receive a portion of the first closure ring, and the first closure ring includes a ridge configured to provide a stop for the first cradle.

Various embodiments are described, wherein when a portion of the first cradle engages the ridge of the first closure ring of the first cradle and the screw hole of the first closure ring align.

Various embodiments are described, wherein when a portion of the first closure ring engages the slot of the first cradle and the screw hole of the first closure ring align.

Various embodiments are described, wherein the slot is formed by a first cradle arm and a first cradle interface surface.

BRIEF DESCRIPTION OF THE DRAWINGS

In order to better understand various exemplary embodiments, reference is made to the accompanying drawings, wherein:

FIGS. 1F, 1G, and 1H illustrate various views where the components of the single rib fixation system are separated;

FIG. 1I illustrates the single rib fixation system affixed to a rib using a screw adjacent to vertebrae;

FIGS. 2A-2D illustrate various perspective views of the rib plate assembly;

FIGS. 4A and 4B illustrate a first embodiment of rib plate that may be used with a tie;

FIGS. 4C and 4D illustrate a second embodiment of rib plate that may be used with a tie;

FIGS. 4E and 4F illustrate a third embodiment of rib plate that may be used with a tie;

FIGS. 4G and 4H illustrate a fourth embodiment of rib plate that may be used with a tie;

FIGS. 10A and 10B illustrate various perspective views of the second cradle;

FIGS. 11A and 11B illustrate various perspective views of the third cradle;

To facilitate understanding, identical reference numerals have been used to designate elements having substantially the same or similar structure and/or substantially the same or similar function.

DETAILED DESCRIPTION

Figure 1A:
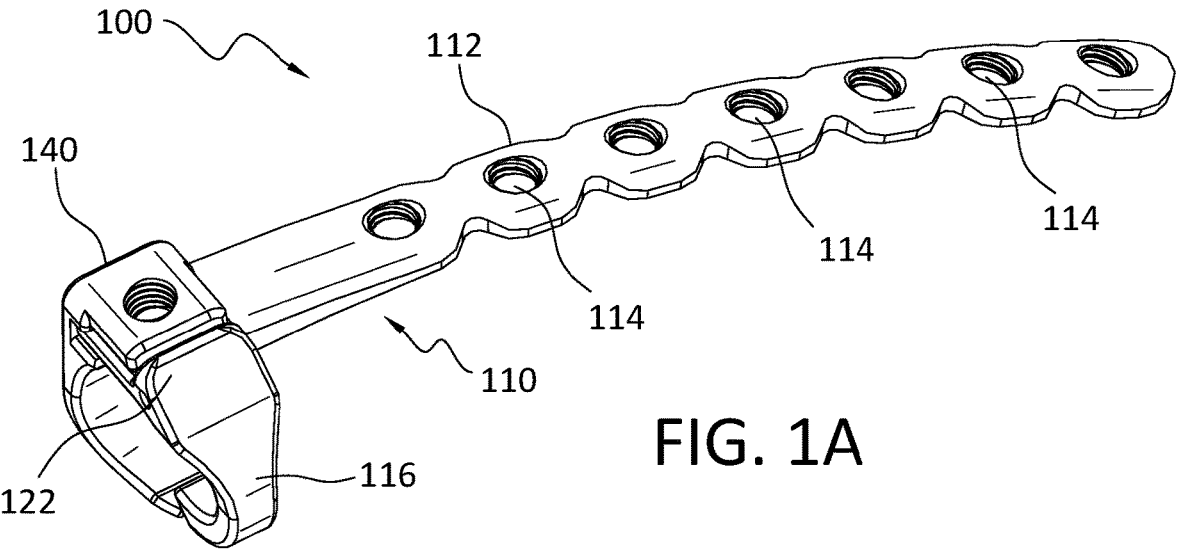
FIGS. 1A and 1B illustrate top and bottom perspective views of the single rib fixation system.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Currently, fractures of the very posterior rib near the vertebrae are difficult to plate due to the limited space available to place screws on the posterior side of the fracture. Typically one or two screws are able to be placed, but three is difficult while staying on the rib (rather than extending up onto the transverse process). Embodiments of a single rib fixation system will be described that will would allow a single screw to be placed on the posterior aspect of the fractures while still providing sufficient stability for healing.

The single rib fixation system utilizes a ring that goes all the way around the rib on the posterior aspect of the fracture and uses one screw to secure the ring to the rib. The ring distributes the load around the rib and along with the screw results in a strong and secure fixation system. A plate attached to the ring extends along the rib and may be secured at various locations based upon the fracture. The system may be placed anywhere on the rib for patients with poor bone quality that would benefit from circumferential fixation. The system may also be used intrathoracically, as the ring design makes it easy to introduce to the intrathoracic space without significant instrumentation. The system may include a ring that is made up of two components that get placed on either side of the rib. A second ring component may have a slot that engages a first ring component and is then held together with a screw through both components. The screw is inserted through both ring components and then into the posterior rib segment of the fracture for fixation. The first ring component may extend into a rib plate (or a universal plate that can be contoured using a bending template) that is fixated with screws on the anterior aspect of the fracture. This approach may take up less space on the rib, reduces the number of screws needed, and provides the same strength as using multiple screws.

In another embodiment of the single rib fixation system a fixation tie, such as a zip tie or cable, may be placed around the rib and the rib plate to secure the plate to the rib. The allows for the plate to be fixed to the rib in locations where a screw may be difficult to place.

In some situations a broken rib may benefit from being stabilized to reduce movement of the rib. Currently, soft tissue may be used to provide stabilization of the broken rib, but another approach is to connect the broken rib to other ribs. In yet another embodiment, concepts of the single rib fixation system may be expanded to allow the single rib fixation system to be connected to other ribs to provide additional stabilization of the rib. This multi-rib fixation system may also be used when there are multiple broken ribs.

The multi-rib fixation system may be a modular system that includes rib rings that extend into plates and vertical struts that span between ribs. For a flail segment, rib rings would be placed on the posterior aspect of each fractured rib, as well as connected to a rib superior and a rib inferior to the flail segment. These rings surround the body of the rib to provide circumferential stability and have a single screw hole for a screw. The connection segments may be placed between each of the rib rings to connect the rings to provide superior/inferior stability of the flail segment. This construct could be built larger or smaller depending on the fracture pattern, thereby providing stability for severe trauma patients. Further, laminar hooks could also be included for inferior stability if the most inferior ribs are fractured or are otherwise unable to provide sufficient stability. This type of system could be used beyond the posterior rib and into the lateral and anterior aspects of the rib for patients with poor quality bone, where the circumferential stability could improve the patient outcome, or when large flail segments require additional stability. This system could also be used intrathoracically for rib flail segment stabilization.

Figure 1B:
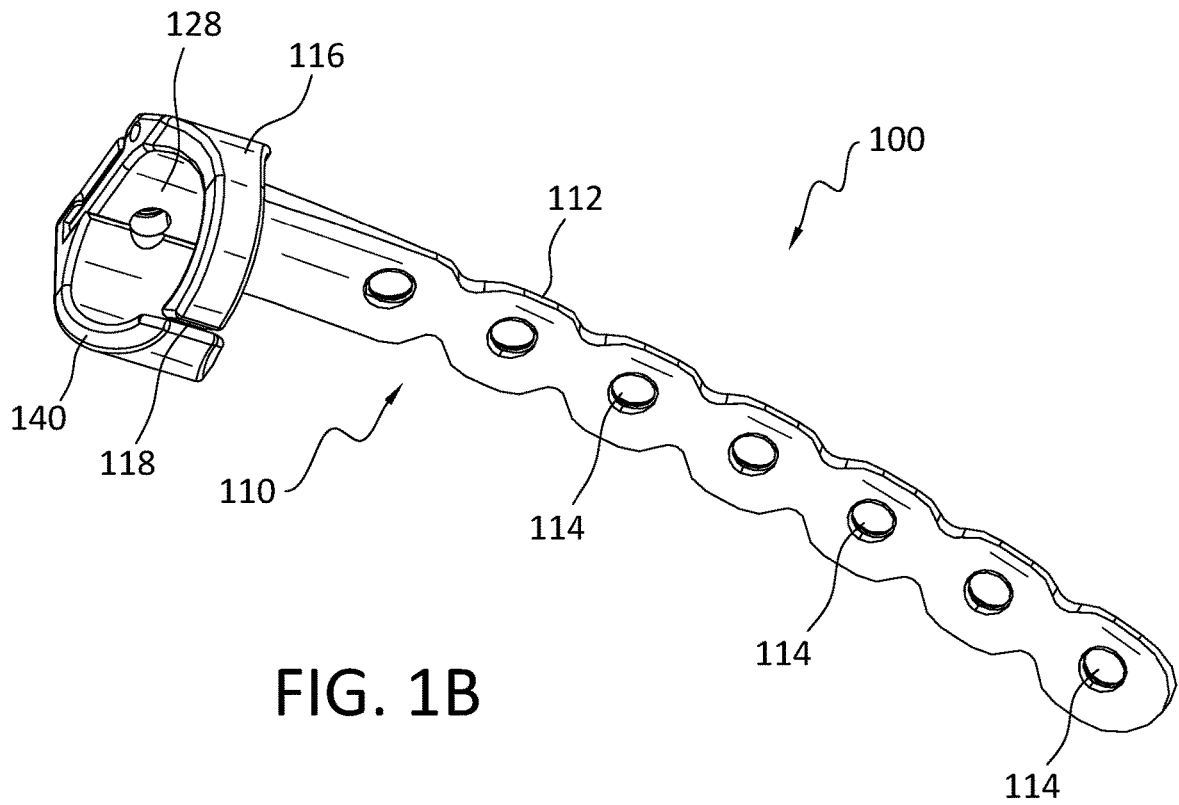
Figures 1C, 1D:
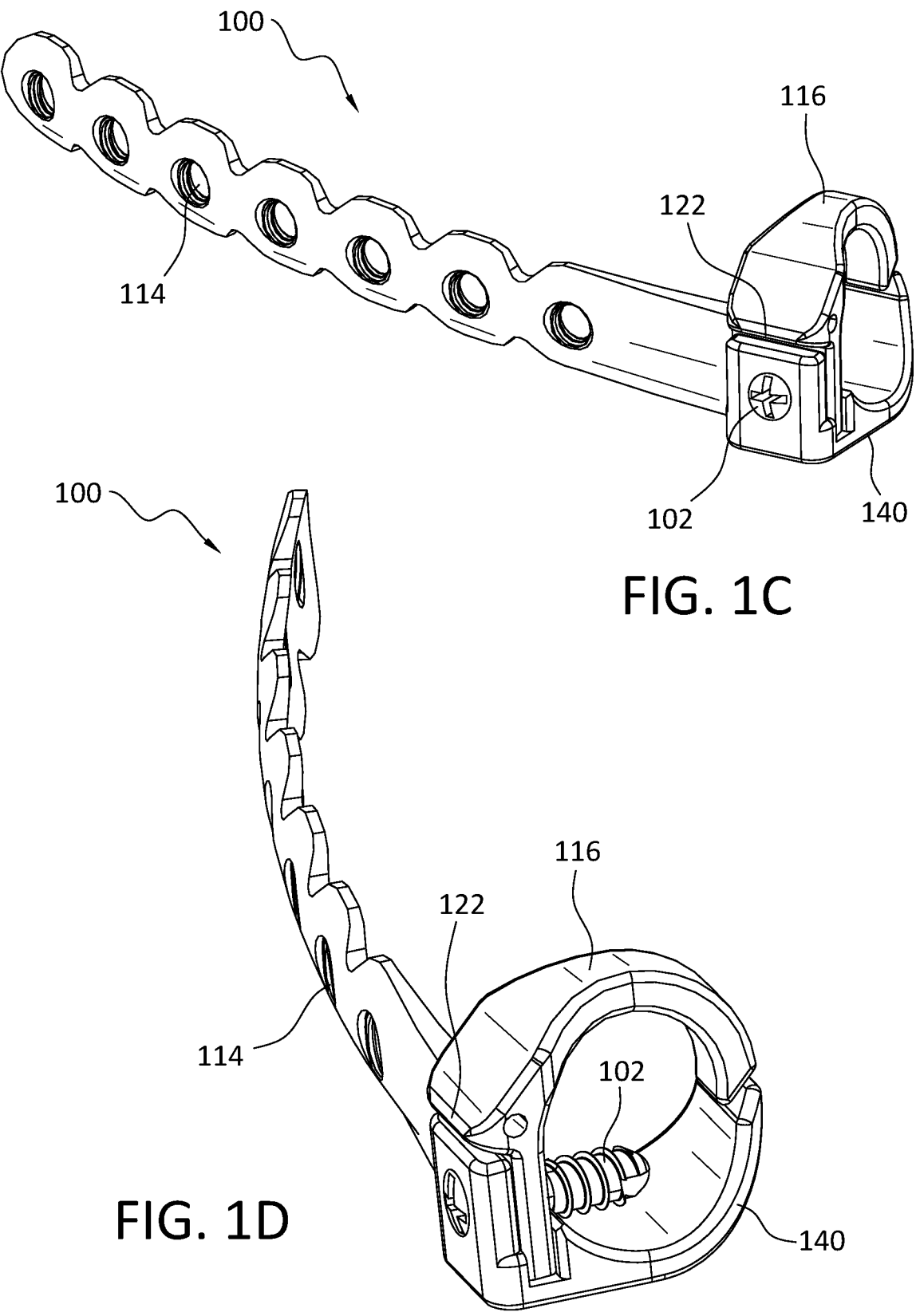
FIGS. 1C and 1D illustrate two different perspective views of the single rib fixation system with a screw.
Figure 1E:
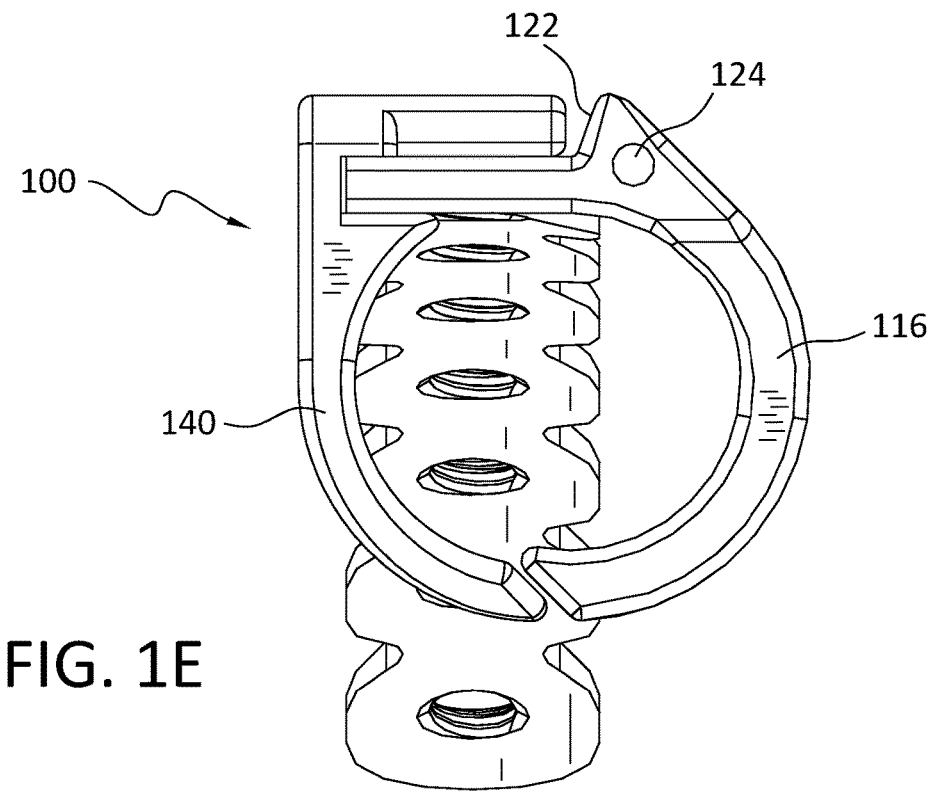
FIG. 1E illustrates an end view of the single rib fixation system.
Figure 1F:
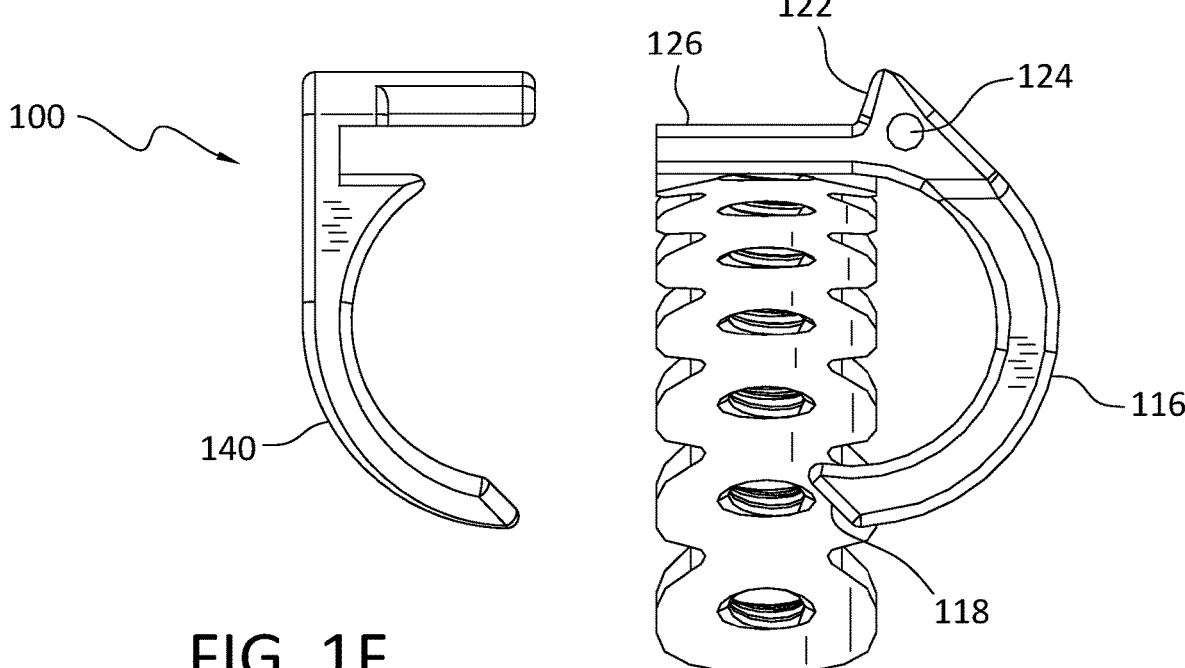
Figure 2C:
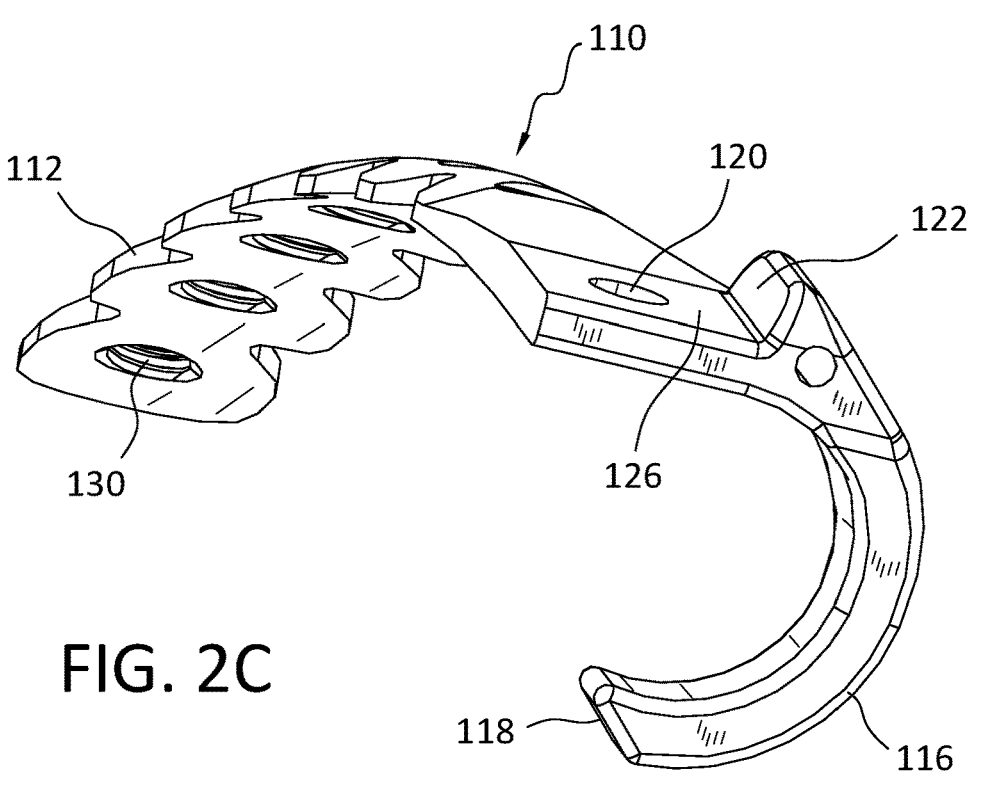
Figure 2D:
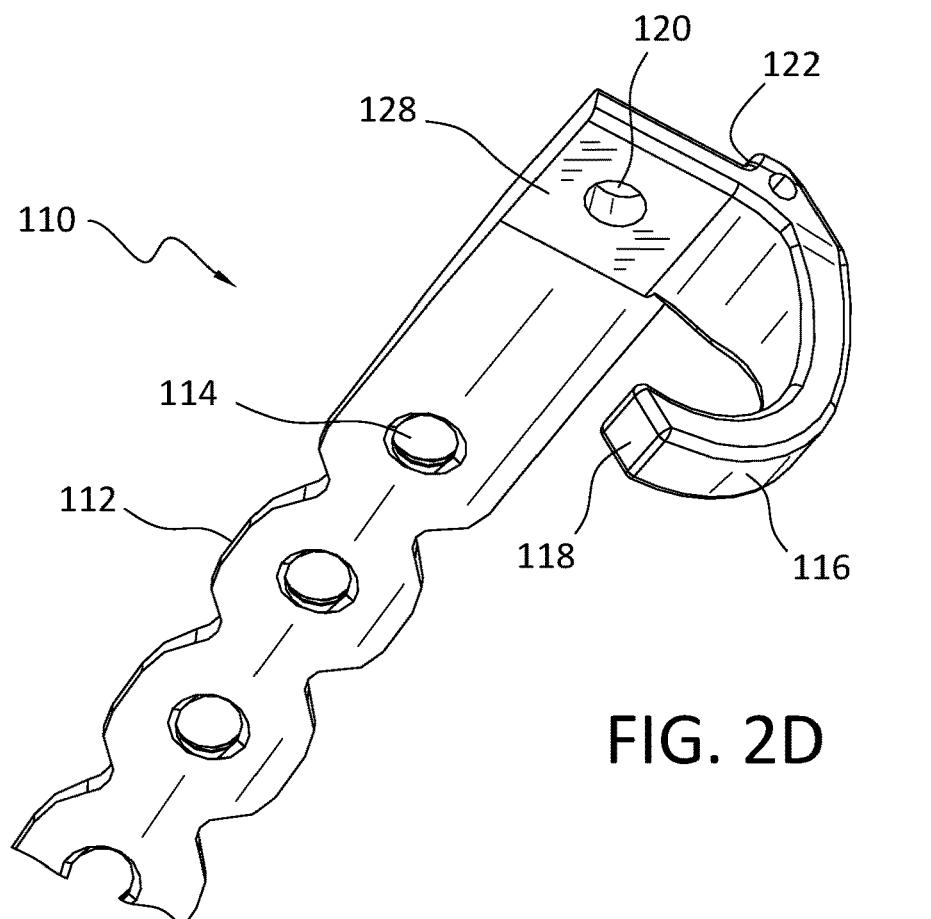

FIGS. 1A and 1B illustrate top and bottom perspective views of the single rib fixation system. FIGS. 1C and 1D illustrate two different perspective views of the single rib fixation system with a screw. FIG. 1E illustrates and end view of the single rib fixation system. FIGS. 1F, 1G, and 1H illustrate various views where the components of the single rib fixation system are separated. FIG. 1I illustrates the single rib fixation system 100 affixed to a rib 104 using a screw adjacent to vertebrae 106.

The single rib fixation system 100 includes a rib plate assembly 110 and a second ring component 140. FIGS. 2A-2D illustrate various perspective views of the rib plate assembly 110. The rib plate assembly 110 includes a rib plate 112 and a first ring component 116. The rib plate 112 extends from the first ring component 116 and may be contoured to match the contour of the rib. Further, the rib plate 112 may be bendable in order to allow the rib plate 112 to be bent to match the contour of the patient's rib where the rib plate 112 is being placed. The rib plate 112 may include a plurality of plate screw holes 114. These plate screw holes 114 provide a variety of locations where the surgeon may insert screws to secure the plate to the fractured rib. These plate screw holes 114 may also be used to capture broken pieces of the rib. The plate screw holes 114 may have plate hole threads 130. These threads 130 may be used with screws that have threaded heads.

Figures 3A, 3B:
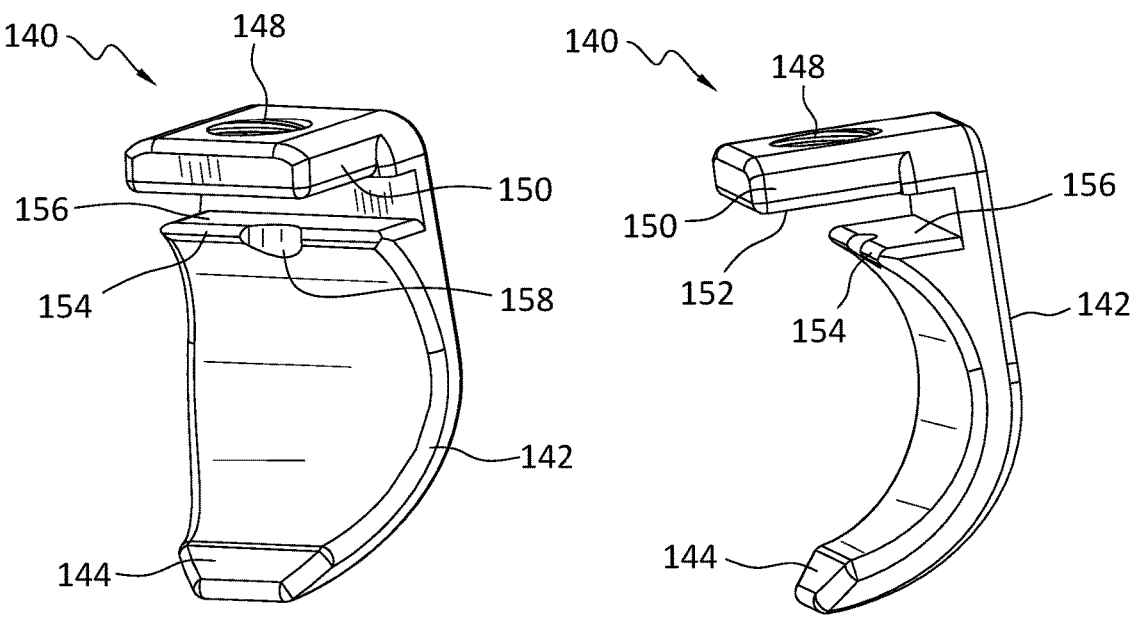
FIGS. 3A-3D illustrate various perspective views of the second ring component.

The first ring component 116 is curved to generally match the shape of the rib and its surrounding tissue. The first ring component includes first ring component distal end 118. The first ring component distal end 118 may engage a distal end of the second ring component 140 to form a ring around the rib. The first ring component 116 may also include rib plate ring top surface 126 and rib plate ring bottom surface 128. The rib plate ring top surface 126 may engage the arm interface surface 152 (see FIG. 3B) of the second ring component 140. The first ring component 116 also has a rib plate ring hole 120 that is configured to receive the screw 102 that secures the rib plate assembly 110 to the rib 104.

Figures 3C, 3D:
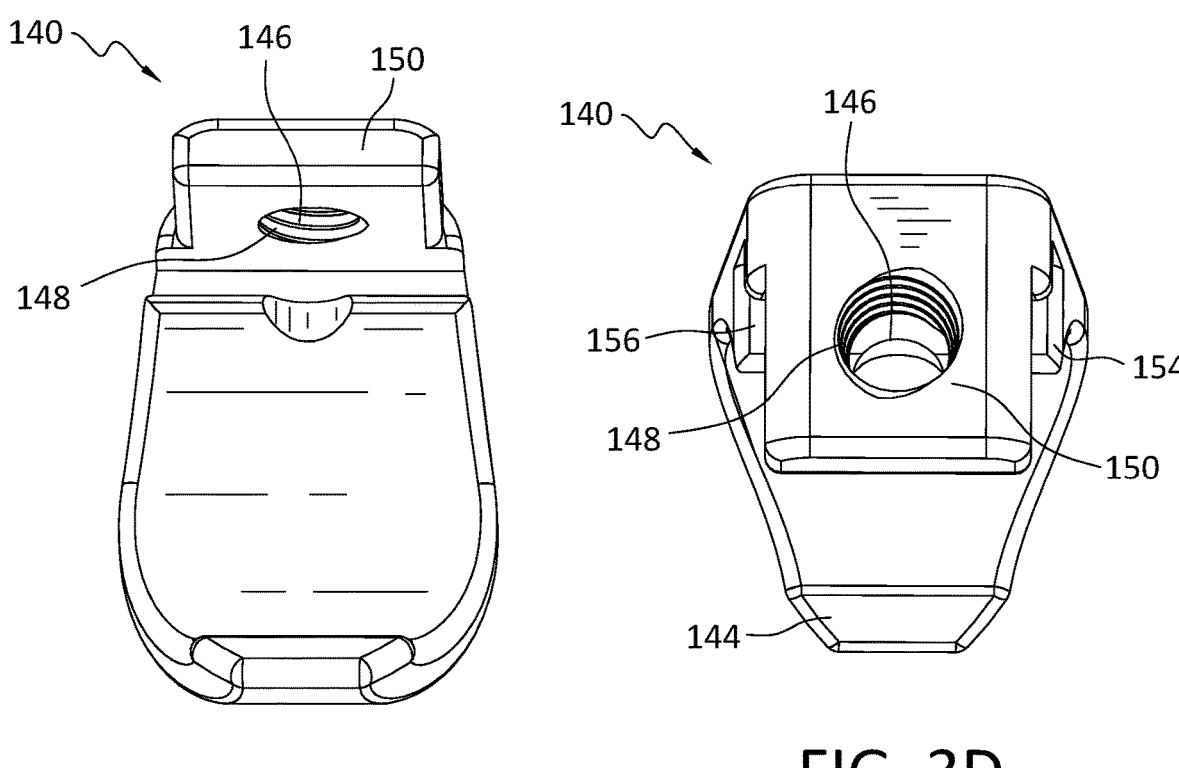

The first ring component 116 includes first ring component ridge 122 that acts as a stop and may engage an end of the second ring component arm 150 (see FIGS. 3A and 3C) of the second ring component 140.

FIGS. 3A-3D illustrate various perspective views of the second ring component 140. The second ring component 140 includes second ring component hook 142 and second ring component arm 150. The second ring component hook 142 has a curved or hooked shape that is curved to generally match the shape of the rib and its surrounding tissue. The second ring component hook 142 has second ring component hook end 144 that is configured to approach and engage first ring component end 118 to form a ring around the rib 104.

The second ring component arm 150 includes second ring component screw hole 146 with second ring component screw hole threads 148. The screw 102 may be inserted in second ring component screw hole 146 and through rib plate ring hole 120 to then engage the rib 104. The screw 102 may have threads on the head that engage second ring component screw hole threads 148. As the screw is tightened, it secures rib plate assembly 110 and second ring component 140 to one another and to the rib 104.

The second ring component arm 150 includes arm interface surface 152 that engages the rib plate ring top surface 126. The second ring component 140 includes hook ridge 154 and hook ridge interface surface 156 that along with second ring component arm 150 form a slot that receives the first ring component 116. The slot may provide a stop to the first ring component 116 that aligns rib plate ring hole 120 and second ring component screw hole 146. The hook ridge interface surface 156 has a screw notch 158a that allows the screw to pass through second ring component screw hole 146 without interference.

The rib plate assembly 110 shows the first ring component 116 integrated with rib plate 112. In other embodiments they may be separate elements. In yet another embodiment, the rib plate 112 may instead be integrated with second ring component 140.

The single rib fixation system 100 may be a part of a surgical kit that may be used to repair and stabilize broke ribs. The kit may contain a plurality of first ring components 116, second ring components 140, and screws 102. These various items may be present in a variety of sizes (e.g., different lengths and widths) to allow for application to different locations on the ribs and to accommodate different sizes of patient anatomy. The first ring component 116 may come with a default curvature that may be further altered by the surgeon during surgery to match the curvature of the rib being treated. Further, the size and curvature of first ring component 116 and second ring component hook 142 may be varied to accommodate different sizes of ribs. The various components of the single rib fixation system 100 may be made of any surgical grade material that may be safely used and that has the strength needed to secure the fractured rib.

In another embodiment, the rib plate 112 and second ring component 140 may be 3D printed based upon the specific patient anatomy and a location chosen by the surgeon. Such an approach allows for very specific customization of the single rib fixation system 100.

The single rib fixation system 100 may be used in a surgical procedure to treat a fractured rib. The surgeon determines a location on the rib 104 where the single rib fixation system 100 will be placed. Then the surgeon determines the size of single rib fixation system 100 to be affixed to the fractured rib based on the location of the rib fracture. The single rib fixation system 100 has a low profile so the ring may be placed close to the vertebrae 106 and not interfere with the transverse process 108. When the ring including first ring component 116 and second ring component hook 142 are placed close to the vertebrae 106, then the ring may encompass soft tissue, such as muscle, nerves, vasculature, etc., along with the bone of the rib 104. The shape of the ring allows for forces applied by the ring to be spread around the soft tissue to reduce these forces and avoid injury to any one soft tissue area. Next, the surgeon determines if the curve of rib plate 112 matches the curve of the rib 104 to be treated. If not, the rib plate 112 may be bent to match the curvature of the rib 104. The surgeon then may place the rib plate 112 on the rib 104. The specific location may be determined and adjusted so that the plate screw holes 114 align with portions of the rib 104 that are capable of receiving a screw. Further, when needed a plate screw hole 114 may be placed over a bone fragment that needs to be captured by a screw 102 so that its position is fixed relative to adjacent bone portions. Then the surgeon may place one or more screws 102 in plate screw holes 114 to secure the rib plate 112 to the rib 104. The surgeon next may place second ring component 140 around the rib 104 and in engagement with first ring component 116 so that the rib plate ring hole 120 and second ring component screw hole 146 align. The second ring component 140 may then be secured to the rib 104 and first ring component 116 using a screw 102. At this point any additional screws 102 may be placed by the surgeon in plate screw holes 114 as needed. This provides for a secure fixation of a plate to a fractured rib. The use of the ring helps to improve this secure fixation and allows for fixation near the vertebrae 106. Note that these various steps may be performed in other orders as well depending upon the surgeon preference.

FIGS. 4A-4H illustrate four different rib plates that may be used with a fixation tie. FIGS. 4A and 4B illustrate a first embodiment of rib plate 212. The rib plate 212 includes a fixation structure that are fixation slots 218 that are configured to receive and secure a fixation tie 216. The fixation tie 216 may a zip tie, wire, or other fixation tie that may be used in medical applications that wrap around a portion of the patients anatomy. The fixation slot 218 may include fixation edges 220. The fixation slot 218 captures the fixation tie 216 and prevents its movement along the length of the rib plate 212. The rib plate 212 may have more than one location with fixation slots 218 that will allow for the use of more than one fixation tie 216. The fixation slots 218 may be located anywhere along the rib plate 212 based upon the requirements of various application of the rib plate 212.

FIGS. 4C and 4D illustrate a second embodiment of rib plate 212. The rib plate 212 includes fixation structures that are fixation openings 222 that are configured to receive and secure a fixation tie 216. The fixation tie 216 may a zip tie, wire, or other fixation tie that may be used in medical applications that wrap around a portion of the patients anatomy. The fixation opening 222 captures the fixation tie 216 and prevents its movement along the length of the rib plate 212. The rib plate 212 may have more than one location with fixation openings 222 that will allow for the use of more than one fixation tie 216. The fixation openings 222 may be located anywhere along the rib plate 212 based upon the requirements of various application of the rib plate 212.

FIGS. 4E and 4F illustrate a third embodiment of rib plate 212. The rib plate 212 includes fixation opening 222 on one side of rib plate 212 and a fixation slot 218 on the other side of the rib plate 212 that are configured to receive and secure a fixation tie 216. The fixation tie 216 may a zip tie, wire, or other fixation tie that may be used in medical applications that wrap around a portion of the patients anatomy. The fixation opening 222 and fixation slot 218 capture the fixation tie 216 and prevents its movement along the length of the rib plate 212. The rib plate 212 may have more than one location with fixation opening 222 and fixation slot 218 that will allow for the use of more than one fixation tie 216. The fixation openings 222 and fixation slots 218 may be located anywhere along the rib plate 212 based upon the requirements of various application of the rib plate 212.

FIGS. 4G and 4H illustrate a fourth embodiment of rib plate 212. The rib plate 212 includes an extension 224 that has fixation structures that are fixation slots 218 that are configured to receive and secure a fixation tie 216. The fixation tie 216 may a zip tie, wire, or other fixation tie that may be used in medical applications that wrap around a portion of the patients anatomy. The fixation slot 218 may include fixation edges 220. The fixation slot 218 captures the fixation tie 216 and prevents its movement along the length of the rib plate 212. The extension may include one or two screw holes. A first screw hold aligns with a plate screw hole 214 of the rib plate 212. A screw 102 is placed through these two screw holes so that the extension 224 is fastened to rib plate 212. The second screw hole is between the fixation slots 218 and is optional. If the second screw hole is present, then a screw may optionally be inserted therethrough into the rib. Then a fixation tie 216 may be placed over the screw 102. In this case the fixation tie 216 will help secure the extension 224 and thereby rib plate 212 to the rib and distribute the forces on the rib around the rib. This is especially beneficial when muscle, nerves, and vasculature are included with the rib within the fixation tie 216. In other embodiments, the fixation structure of the fixation edge 220 may be fixation openings 222 or a combination of a fixation opening 222 and a fixation slot 218. The rib plate 212 illustrated in FIGS. 4G and 4H do not have fixation slots 218 or fixation openings 222, but in alternative embodiments the rib plates 212 may include these elements as illustrated above in the first, second, and third embodiments of the rib plate 212.

The use of the fixation tie 216 provides the benefit of securing the rib plate 212 to the rib without the use of a screw. It also provides fixation when it is difficult to place at least three screws and allows for the placement of the plate close to the transverse process 108.

Figure 5A:
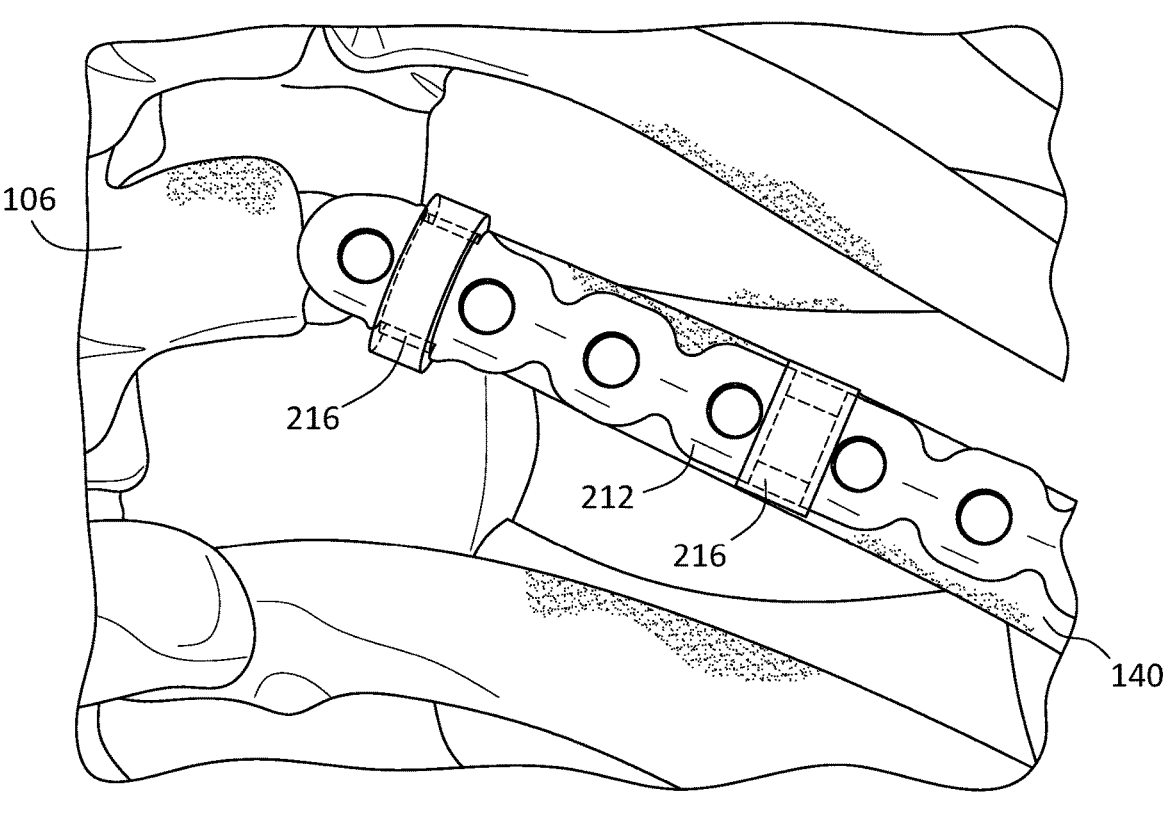
FIG. 5A illustrates an embodiment of the rib plate attached to a rib using fixation tie.
Figure 5B:
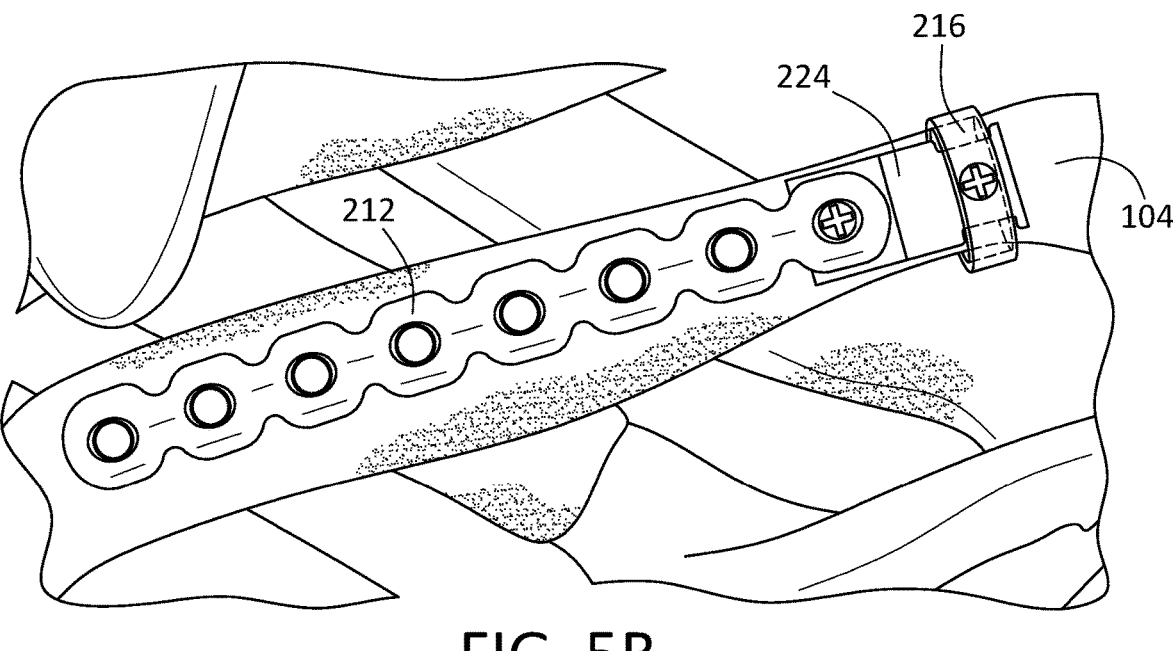
FIG. 5B illustrates an embodiment of the rib plate with extension attached to a rib using fixation tie.

FIG. 5A illustrates an embodiment of the rib plate 212 attached to a rib 104 using fixation tie 216. FIG. 5B illustrates an embodiment of the rib plate 212 with extension 224 attached to a rib 104 using fixation tie 216.

The rib plate 212 may be part of a kit with various sizes of rib plates 212. The kit may also include additional extensions 224, screws 102 and fixation ties 216 of various sizes as well. Further, the rib plate 212 may be 3D printed to match the patient anatomy in other embodiments.

The various embodiments of rib plate 212 may be used in a surgical procedure to treat a fractured rib. The surgeon determines a location on the rib 104 where the rib plate 212 will be placed. Then the surgeon determines the size of rib plate 212 to be affixed to the fractured rib based on the location of the rib fracture. The rib plate 212 has a low profile so the ring may be placed close to the vertebrae 106 and not interfere with the transverse process 108. When the fixation tie 216 is placed close to the vertebrae 106, then the fixation tie 216 may encompass soft tissue, such as muscle, nerves, vasculature, etc., along with the bone of the rib 104. The fixation tie 216 allows for forces applied by the ring to be spread around the soft tissue to reduce these forces to avoid injury. Next, the surgeon determines if the curve of rib plate 212 matches the curve of the rib 104 to be treated. If not, the rib plate 212 may be bent to match the curvature of the rib 104. The surgeon then may place the rib plate 212 on the rib 104. The specific location may be determined and adjusted so that the plate screw holes 214 align with portions of the rib 104 that are capable of receiving a screw. Further, when needed a plate screw hole 214 may be placed over a bone fragment that needs to be captured by a screw 102 so that its position is fixed relative to adjacent bone portions. Then the surgeon may place one or more screws 102 in plate screw holes 214 to secure the rib plate 212 to the rib 104. If the extension 224 is used, then the surgeon may put the extension 224 in place and place a screw through the rib plate 212 and the extension 224 to secure them to the rib 104 and to one another. Also, a second screw may optionally be placed through the second hole in the extension 224. The surgeon next may place fixation tie 216 around the rib 104 and the rib plate 212 (or extension 224 if used). At this point any additional screws 102 may be placed by the surgeon in plate screw holes 114 as needed. This provides for a secure fixation of a plate to a fractured rib. The use of the fixation tie 216 helps to improve this secure fixation and allows for fixation near the vertebrae 106.

FIGS. 1I, 5A, and 5B illustrate rib plates attached to the exterior of the rib 104. In other embodiments, the rib plates may be attached intrathoracically on the interior of the rib 104.

Figures 6A, 6B:
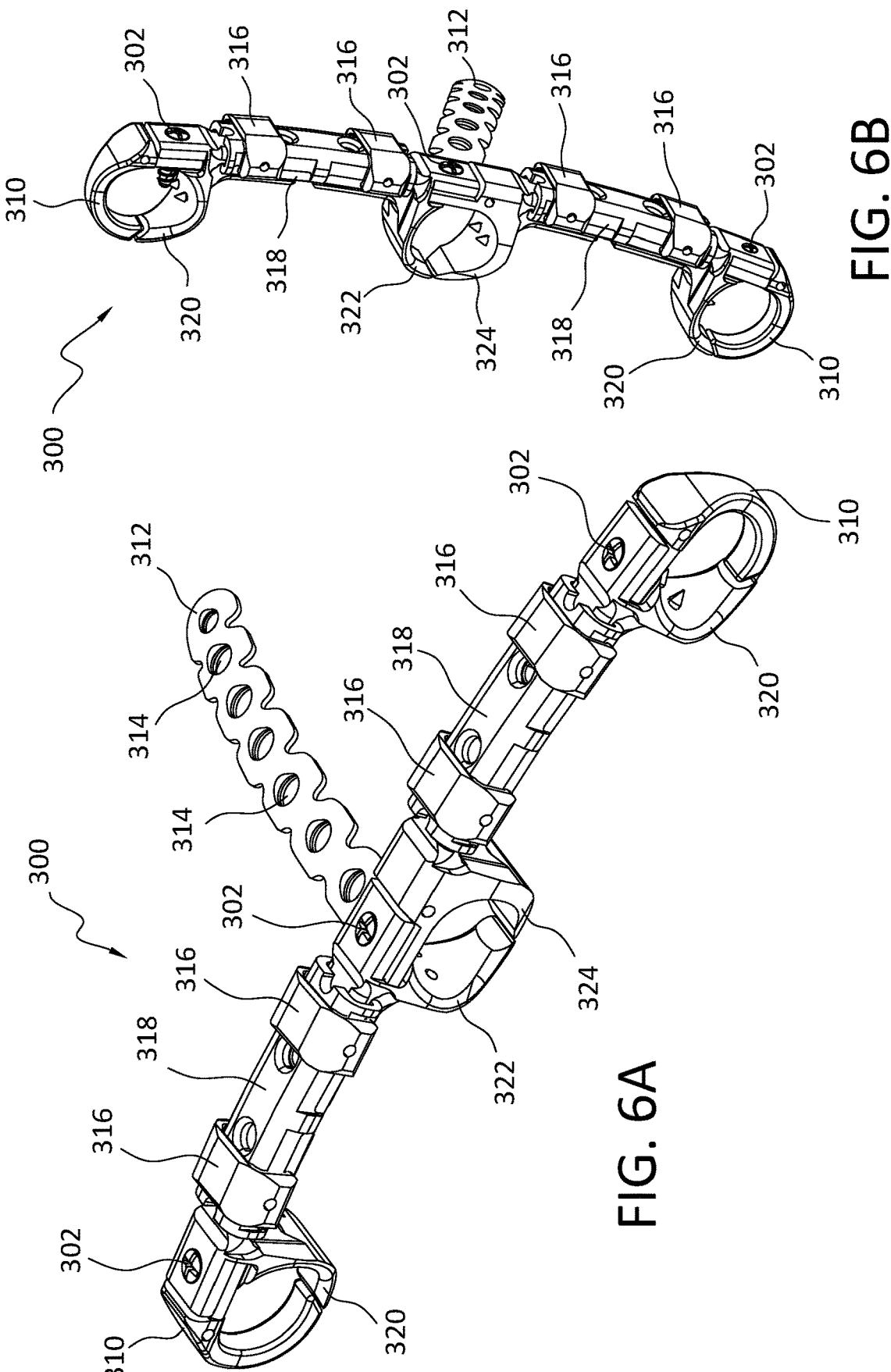
FIGS. 6A and 6B illustrate an embodiment of multi-rib fixation system.

FIGS. 6A and 6B illustrate an embodiment of multi-rib fixation system. The multi-rib fixation system 300 includes a rib plate 312 with plate screw holes 314. The rib plate 312 is connected to an assembly that vertically spans more than one rib of the patient. In FIGS. 6A-B, the multi-rib fixation system 300 includes three rings that connect to ribs, and the three rings are connected to one another by spanning segments 318. Providing a connection from a fractured rib to one or more nearby ribs provides increased stability for the fractured rib.

The multi-rib fixation system 300 includes closure ring 310 and first cradle 320 that form a ring around nearby ribs. First cradle 320 is connected to one end of the spanning segment 318. The other end of the spanning segment 318 is connected to either the second cradle 322 or the third cradle 324. Locking clips 316 may be used to connect the spanning segment 318 to first cradle 320, second cradle 322, and third cradle 324. The second cradle 322 and third cradle 324 form a ring that engages the fractured rib and rib plate 312.

Figure 7:
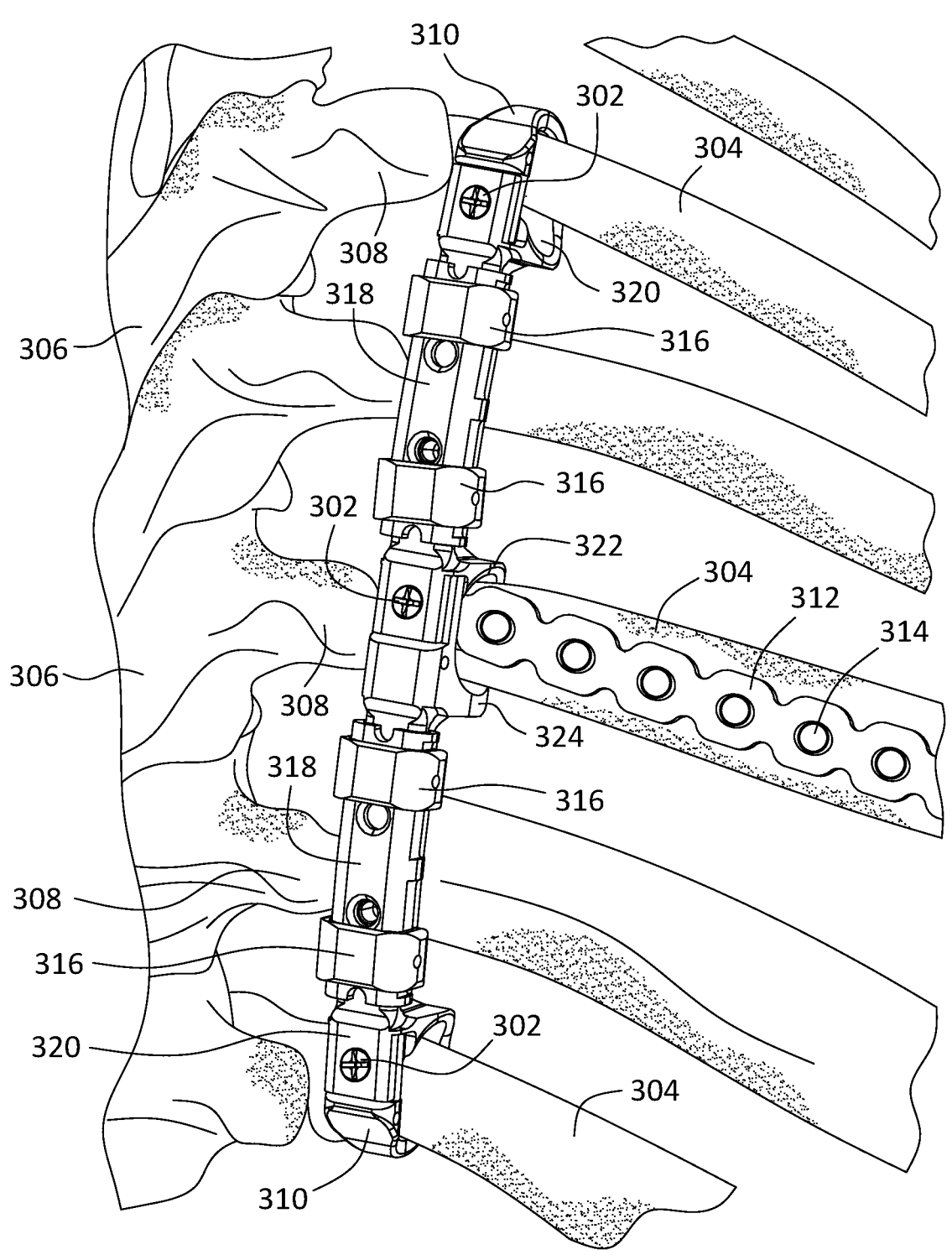
FIG. 7 illustrates the multi-rib fixation system attached to a fractured rib and nearby ribs.

FIG. 7 illustrates the multi-rib fixation system attached to a fractured rib and nearby ribs. The second cradle 322 and third cradle 324 form a ring around the fractured rib 304 and they are connected to the rib plate 312. A screw 302 is placed through the second cradle 322, third cradle 324, and plate screw holes 314 in the rib plate 312 to attach this assembly to the fractured rib 304. Additional screws 302 (not shown) may be placed in plate screw holes 314 to further secure the rib plate 312 to the fractured rib 304. Two additional rings formed by closure ring 310 and first cradle 320 are placed around nearby ribs 304. The closure ring 310 and first cradle 320 may be secured to the nearby rib by screw 302. The first cradle 320 is also connected to the spanning segment 318. The other end of the spanning segment 318 may be connected to one of second cradle 322 and third cradle 324. The locking clip 316 secures the connection between the cradles and spanning segment 318. The installation of the multi-rib fixation system 300 is shown as very close to the vertebrae 306 of the patient. The low profile design of the multi-rib fixation system 300 allows for this positioning and avoids interfering with the transverse process 308. Further, the multi-rib fixation system 300 may be adapted to attach to any nearby rib because various length spanning segments 318 may be used to attach to nearby ribs.

Figures 8A, 8B, 9A, 9B:
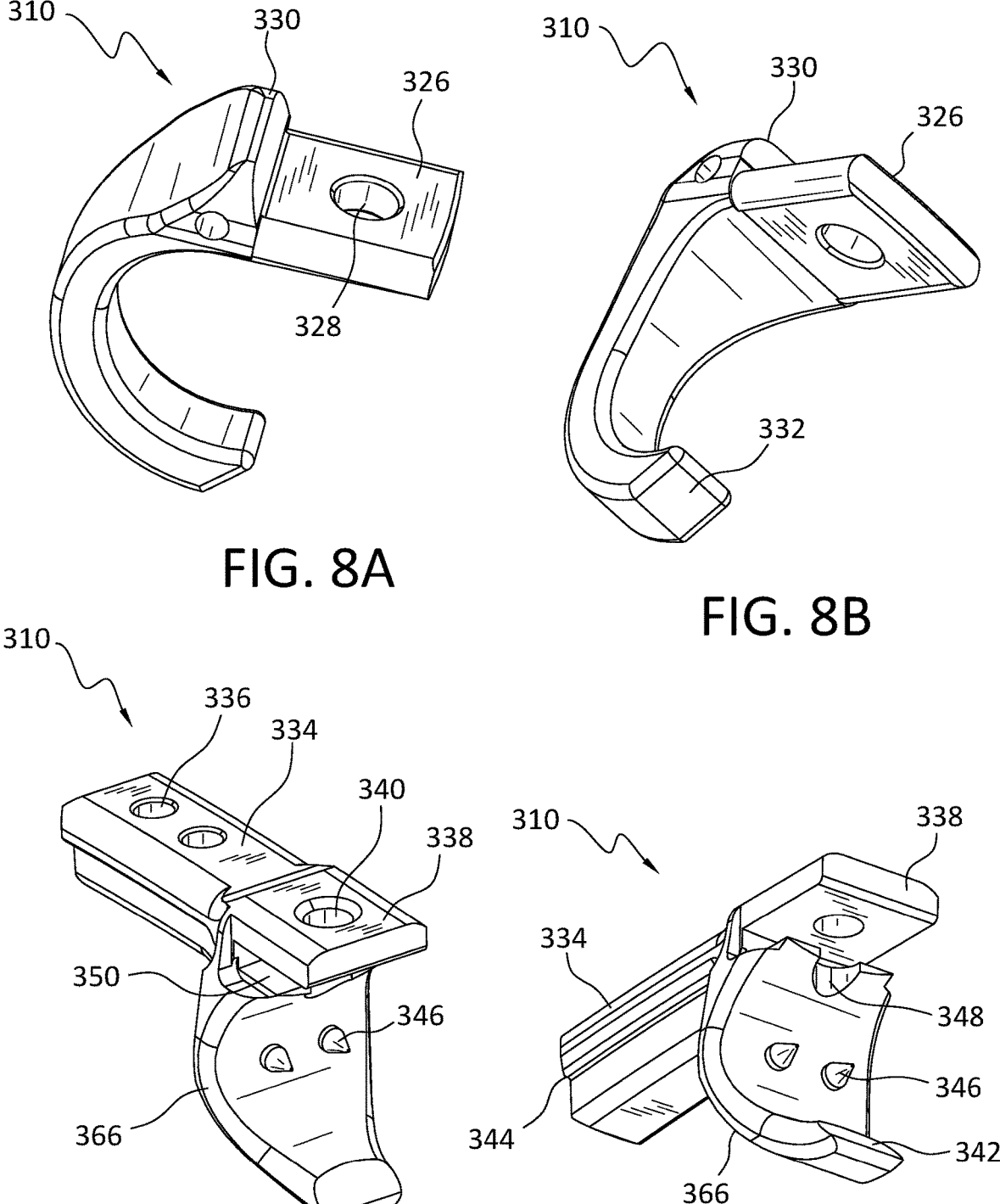
FIGS. 8A and 8B illustrate perspective views of closure ring.
FIGS. 9A and 9B illustrate various perspective views of first cradle.

FIGS. 8A and 8B illustrate perspective views of closure ring 310. The closure ring has a generally semicircular shape that helps to form a ring around the rib 304 in conjunction with first cradle 320. The closure ring 310 includes a closure ring end 332 that interfaces with cradle end 342 (see FIGS. 9A and 9B) to form the ring around the rib. The closure ring 310 also includes closure ring arm 326. The closure ring arm 326 overlaps and interfaces with the cradle arm 338 of first cradle 320. The closure ring arm 326 includes closure ring screw hole 328. The closure ring screw hole 328 aligns with cradle screw hole 340 of the first cradle 320, and a screw is placed through these holes to secure the closure ring 310 and first cradle 320 to one another and the rib 304. A closure ring ridge 330 may help to align closure ring screw hole 328 and cradle screw hole 340 by providing a stop for an end of cradle arm 338 (see FIGS. 9A and 9B) of first cradle 320.

FIGS. 9A and 9B illustrate various perspective views of the first cradle. The first cradle 320 includes cradle hook 366 and cradle arm 338. The cradle hook 366 has a curved or hooked shape that is curved to generally match the shape of the rib and its surrounding tissue. The cradle hook 366 has cradle end 342 that is configured to approach and engage closure ring end 332 to form a ring around the rib. The cradle hook 366 may also include bone spikes 346 that are configured to engage the rib 304.

The cradle arm 338 includes cradle screw hole 340 that may have screw hole threads (not shown). The screw 302 may be inserted in cradle screw hole 340 and through closure ring screw hole 328 to then engage the rib. The screw 302 may have threads on the head that engage cradle screw hole threads. As the screw is tightened, it secures closure ring 310 and first cradle 320 to one another and to the rib 304.

The cradle arm 338 includes a lower surface that engages closure ring arm 326. The first cradle 320 includes interface surface 350 that with cradle arm 338 form a slot that receives the closure ring arm 326. The first cradle 320 has a screw hole indent 348 that allows the screw to pass through cradle screw hole 340 without interference.

The first cradle 320 includes cradle mount 334 that is configured to engage the spanning segment 318. The cradle mount 334 includes mount ledge 344 that defines a portion of the cradle mount 334 that slides into the spanning segment slot 354 (see FIGS. 12A and 12B). Further, the cradle mount 334 includes mount holes 336 that are configured to receive locking clip post 360 (see FIGS. 13A and 13B).

FIGS. 10A and 10B illustrate various perspective views of the second cradle. The second cradle 322 includes cradle hook 366 and cradle arm 338. The cradle hook 366 has a curved or hooked shape that is curved to generally match the shape of the rib and its surrounding tissue. The cradle hook 366 has cradle end 342 that is configured to approach and engage closure ring end 332 to form a ring around the rib. The cradle hook 366 may also include bone spikes (not shown) that are configured to engage the rib 304.

The cradle arm 338 includes cradle screw hole 340 that may have screw hole threads (not shown). The screw 302 may be inserted in cradle screw hole 340 and through cradle screw hole 340 of the third cradle 324 to then engage the rib. The screw 302 may have threads on the head that engage cradle screw hole threads. As the screw is tightened, it secures second cradle 322 and third cradle 324 to one another and to the rib 304.

The cradle arm 338 includes a lower surface that engages the cradle arm 338 of third cradle 324. The second cradle 322 includes interface surface 350 that with cradle arm 338 form a slot that receives the cradle arm 338 of third cradle 324. The slot may provide a stop to the cradle arm 338 of third cradle 324 that aligns cradle screw holes 340 of the second cradle and cradle screw holes 340 of the third cradle. The second cradle 322 has a screw hole indent 348 that allows the screw to pass through cradle screw hole 340 without interference.

The second cradle 322 includes cradle mount 334 that is configured to engage the spanning segment 318. The cradle mount 334 includes mount ledge 344 that defines a portion of the cradle mount 334 that slides into the spanning segment slot 354 (see FIGS. 12A and 12B). Further, the cradle mount 334 includes mount holes 336 that are configured to receive locking clip post 360 (see FIGS. 13A and 13B).

FIGS. 11A and 11B illustrate various perspective views of the third cradle. The third cradle 324 includes cradle hook 366 and cradle arm 338. The cradle hook 366 has a curved or hooked shape that is curved to generally match the shape of the rib and its surrounding tissue. The cradle hook 366 has cradle end 342 that is configured to approach and engage closure ring end 332 to form a ring around the rib. The cradle hook 366 may also include bone spikes 346 that are configured to engage the rib 304.

The cradle arm 338 includes cradle screw hole 340 that may have screw hole threads (not shown). The screw 302 may be inserted in cradle screw hole 340 and through cradle screw hole 340 of the second cradle 322 to then engage the rib. The screw 302 may have threads on the head that engage cradle screw hole threads of the place second cradle 322. As the screw is tightened, it secures second cradle 322 and third cradle 324 to one another and to the rib 304.

The third cradle 324 includes cradle ridge 364. The cradle ridge 364 may help to align the cradle screw holes 340 of the second cradle 322 and third cradle 324 by providing a stop for an end of cradle arm 338 of second cradle 322.

The third cradle 324 includes cradle mount 334 that is configured to engage the spanning segment 318. The cradle mount 334 includes mount ledge 344 that defines a portion of the cradle mount 334 that slides into the spanning segment slot 354 (see FIGS. 12A and 12B). Further, the cradle mount 334 includes mount holes 336 that are configured to receive locking clip post 360 (see FIGS. 13A and 13B).

Figures 12A, 12B, 13A, 13B:
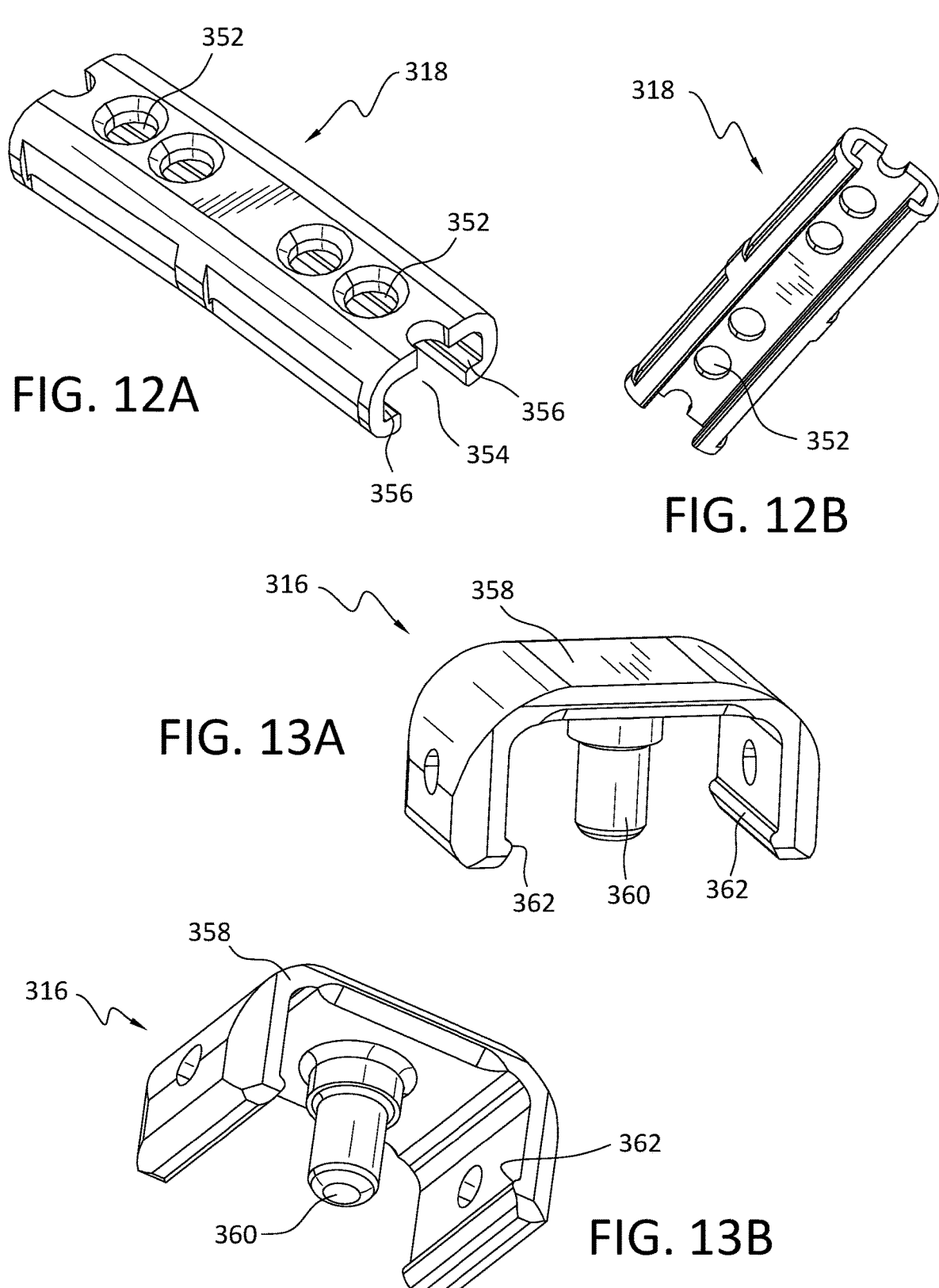
FIGS. 12A and 12B illustrate perspective views of spanning segment.
FIGS. 13A and 13B illustrate perspective views of locking clip.

FIGS. 12A and 12B illustrate perspective views of spanning segment. The spanning segment 318 has a generally rounded rectangular tubular shape. The spanning segment 318 can take other shapes as well. Along the top of the spanning segment 318 are a number of spanning segment holes 352. As described above the spanning segment holes 352 receive the locking clip post 360 (see FIGS. 13A and 13B). In this example four spanning segment holes 352 are illustrated, but the spanning segment 318 may include more or fewer holes. The bottom of the spanning segment 318 has a spanning segment slot 354. This results in the spanning segment 318 being an open tube. The central opening of spanning segment 318 and the spanning segment slot 354 are configured to receive the cradle mount 334 of the first cradle 320, second cradle 322, and third cradle 324. The mount ledge 344 may interface with spanning segment ledge 356. The spanning segment ledge 356 is on the inside of spanning segment 318 adjacent the spanning segment slot 354. The spanning segment 318 may take on various lengths and may have various number of holes. This allows for the multi-rib fixation system 300 to be attached to different ribs according to the patient anatomy.

FIGS. 13A and 13B illustrate perspective views of locking clip. The clips 316 may include a generally U-shaped body 358. The shape of the body 348 is configured to be complementary to the shape of the spanning segment 318. This allows for the locking clip 316 to be clipped onto the spanning segment 318. The locking clip 316 includes locking clip ledges 362 on the inside of the locking clip 316 that are configured to engage the spanning segment 318. The locking clip 316 includes locking clip post 360 that is placed in spanning segment hole 352 and mount hole 336. Accordingly, when the locking clip 316 is clipped onto the locking clip 316 that is connected to cradle mount 334, the locking clip 316 secures the spanning segment 318 to the cradle mount 334 of the cradles. It is noted that the locking clip post 360 may have a stepped shape where a larger diameter portion close to the locking clip body 358 engages the spanning segment hole 352 and the smaller diameter portion distal from the locking clip body 358 engages the mount hole 336. In this situation the spanning segment hole 352 and mount hole 336 have different diameters. On other embodiments they may have the same diameter and the diameter of locking clip post 360 may constant along its length.

In other embodiments, the spanning segments 318 may be connected to the cradles using other fasteners, for example, screws, pins, fixation ties, etc. In yet another embodiment the spanning segments 318 may be connected to the cradles using releasable connections, such a ball and detent structure, a coiled circular sprint and detent structure, etc.

The various components of the multi-rib fixation system 300 may be included in a kit to be used to assemble the multi-rib fixation system 300 to meet the specific needs of the patient. The kit may include closure rings 310, first cradle 320, second cradle 322, and third cradle 324 of various sizes to accommodate different rib sizes. Further, the kit may include a variety of spanning segments 318 with different lengths to allow the multi-rib fixation system 300 to attached to different nearby ribs. The bone spike 346 in the cradles may be removable so that the cradles may be used without them. In another embodiment, only one nearby rib will be used to stabilize a fractured rib. In this situation either the second cradle 322 or the third cradle 324 may not include the cradle mount 334 because no extension is needed.

In other embodiments, the rib plate 312 may be formed integral with either the second cradle 322 or the third cradle 324. This embodiment would reduce the number of elements needed for the multi-rib fixation system 300.

The various components of the multi-rib fixation system 300 may be made of any surgical grade material that may be safely used and that has the strength needed to secure the fractured rib.

In another embodiment, some of the components of the multi-rib fixation system 300 may be 3D printed based upon the specific patient anatomy and a location chosen by the surgeon. Such an approach allows for very specific customization of the multi-rib fixation system 300.

The multi-rib fixation system 300 may be used in a surgical procedure to treat a fractured rib. The surgeon determines a location on the rib 304 where the rib plate 312 will be placed. Then the surgeon determines the size of rib plate 312 to be affixed to the fractured rib based on the location of the rib fracture.

The multi-rib fixation system 300 has a low profile so the ring formed by second cradle 322 and third cradle 324 may be placed close to the vertebrae 306 and not interfere with the transverse process 308. When the ring including first ring second cradle 322 and third cradle 324 are placed close to the vertebrae 306, then the ring may encompass soft tissue, such as muscle, nerves, vasculature, etc., along with the bone of the rib 304. The shape of the ring allows for forces applied by the ring to be spread around the soft tissue to reduce these forces to avoid injury. Next, the surgeon determines if the curve of rib plate 312 matches the curve of the rib 304 to be treated. If not, the rib plate 312 may be bent to match the curvature of the rib 304. The surgeon then may place the rib plate 312 on the rib 304. The specific location may be determined and adjusted so that the plate screw holes 314 align with portions of the rib 304 that are capable of receiving a screw. Further, when needed a plate screw hole 314 may be placed over a bone fragment that needs to be captured by a screw 302 so that its position is fixed to adjacent bone portions. Then the surgeon may place one or more screws 302 in plate screw holes 314 to secure the rib plate 312 to the rib 304. The surgeon next may place second cradle 322 and third cradle 324 around the rib 304 and in engagement with rib plate 312 so that the cradle screw holes 340 and a plate screw hole 314 align. The second cradle 322 and third cradle 324 may then be secured to the rib 304 and rib plate 312 using a screw 302. At this point any additional screws 302 may be placed by the surgeon in plate screw holes 314 as needed. This provides for a secure fixation of a plate to a fractured rib. The use of the ring helps to improve this secure fixation and allows for fixation near the vertebrae 306. Next, the surgeon may attach a spanning segment 318 to a first cradle 320. This assembly may then be placed on the cradle mount 334 of the second cradle 322 so that the first cradle 320 comes into contact with and adjacent rib. Then a closure ring 310 may be placed over the nearby rib and in contact with first cradle 320. Then a screw 302 may be placed in the closure ring screw hole 328 and cradle screw hole 340 of first cradle 320 to secure them to the rib. Further, clips 316 may be placed over the spanning segment 318 to secure the spanning segment 318 to first cradle 320 and second cradle 322. The same procedure may then be repeated for providing a connection between the third cradle 324 and another nearby rib. Note that variations of these steps may be carried out in other orders based upon the specific application of multi-rib fixation system 300 and the preferences of the surgeon.

Further it is noted, that various specific shapes of the various components of the embodiments are disclosed herein. These various components may take on other shapes as well to carry out the function of stabilizing fractured ribs.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A rib fixation system, comprising:
a rib plate having a plurality of screw holes;
a first closure ring with a screw hole;
a first cradle with a screw hole and a cradle mount configured to engage the first closure ring to form a first ring;
a second cradle with a screw hole and cradle mount;
a third cradle with a screw hole configured to engage the second cradle to form a second ring, wherein the second ring is configured to engage the rib plate;
a first spanning segment configured to securely engage the cradle mount of the first cradle and the cradle mount of the second cradle;
a first screw configured to be inserted through the screw hole of the first closure ring and the screw hole of the first cradle; and
a second screw configured to be inserted through the screw hole of the first cradle and the screw hole of the second cradle.

2. The rib fixation system of claim 1, further comprising:
a second closure ring with a screw hole;
a fourth cradle with a screw hole and a cradle mount configured to engage the second closure ring to form a third ring;
a second spanning segment configured to securely engage the cradle mount of the fourth cradle and a cradle mount of the third cradle; and
a third screw configured to be inserted through the screw hole of the second closure ring and the screw hole of the fourth cradle.

3. The rib fixation system of claim 1, further comprising a locking clip configured to secure the first spanning segment to the first cradle.

4. The rib fixation system of claim 1, wherein
the first spanning segment includes a plurality of holes,
the cradle mount of the first cradle includes a hole, and
the locking clip includes a post, wherein the post is configured to be inserted into one of the plurality of holes of the first spanning segment and the hole of the cradle mount of the first cradle.

5. The rib fixation system of claim 1, wherein
the second cradle includes a slot configured to receive a portion of the third cradle, and
the third cradle includes a ridge configured to provide a stop for the second cradle.

6. The rib fixation system of claim 5, wherein when a portion of the second cradle engages the ridge of the third cradle of the second cradle and the screw hole of the third cradle align.

7. The rib fixation system of claim 5, wherein when a portion of the third cradle engages the slot of the second cradle and the screw hole of the third cradle align.

8. The rib fixation system of claim 5, wherein the slot is formed by a second cradle arm and a second cradle interface surface.

9. The rib fixation system of claim 1, wherein the first cradle includes a slot configured to receive a portion of the first closure ring, and the first closure ring includes a ridge configured to provide a stop for the first cradle.

10. The rib fixation system of claim 9, wherein when a portion of the first cradle engages the ridge of the first closure ring of the first cradle and the screw hole of the first closure ring align.

11. The rib fixation system of claim 9, wherein when a portion of the first closure ring engages the slot of the first cradle and the screw hole of the first closure ring align.

12. The rib fixation system of claim 9, wherein the slot is formed by a first cradle arm and a first cradle interface surface.

* * * * *